United States Patent
De Haen et al.

(10) Patent No.: US 6,803,030 B2
(45) Date of Patent: Oct. 12, 2004

(54) BILE ACIDS CONJUGATES WITH METAL ION CHELATES AND THE USE THEREOF

(75) Inventors: Christoph De Haen, Milan (IT); Andrea Beltrami, Milan (IT); Enrico Cappelletti, Milan (IT); Luciano Lattuada, Milan (IT); Mario Virtuani, Milan (IT)

(73) Assignee: Bracco Imaging S.p.A., Milan (IT)

( * ) Notice: Subject to any disclaimer, the term of this patent is extended or adjusted under 35 U.S.C. 154(b) by 0 days.

(21) Appl. No.: 10/220,048

(22) PCT Filed: Feb. 21, 2001

(86) PCT No.: PCT/EP01/01971

§ 371 (c)(1),
(2), (4) Date: Aug. 27, 2002

(87) PCT Pub. No.: WO01/64708

PCT Pub. Date: Sep. 7, 2001

(65) Prior Publication Data

US 2003/0113265 A1 Jun. 19, 2003

(30) Foreign Application Priority Data

Feb. 29, 2000 (IT) .................................. MI2000A0383

(51) Int. Cl.$^7$ ............................ A61B 5/055; C07J 9/00; A61K 31/58
(52) U.S. Cl. ........................... 424/9.323; 424/9.364; 424/9.365; 514/172; 540/3; 552/549; 552/551
(58) Field of Search .................... 424/9.323, 9.364, 424/9.365, 9.363; 514/172; 540/3, 474; 552/549, 551

(56) References Cited

U.S. PATENT DOCUMENTS 6,461,588 B1 * 10/2002 Anelli et al. ............. 424/9.365

FOREIGN PATENT DOCUMENTS

| EP | 0 279 307 A | 8/1988 |
|----|-------------|--------|
| WO | WO 95/19186 | 7/1995 |
| WO | WO 95/28966 | 11/1995 |
| WO | WO 95/32741 | 12/1995 |
| WO | WO 97/32862 | 9/1997 |

OTHER PUBLICATIONS

Oussaid et al, "New Microwave Method for Synthesis of Pyrroles" Canadian Journal of Chemistry, vol. 72(12), p. 2483–2485 (1994).*

Betebenner et al, "Hepatobiliary Delivery of Polyaminopolycarboxylate Chelates: Synthesis and Characterization of a Cholic Acid Conjugate of EDTA and Biodistribution and Imaging Studies with Its Indium–111 Chelate", *Bioconjugate Chem.*, Americal Chemical Society, Washington, US, vol. 2, No. 2, 1991, pp. 117–123.

* cited by examiner

*Primary Examiner*—Richard L. Raymond
*Assistant Examiner*—Zachary C. Tucker
(74) *Attorney, Agent, or Firm*—Nixon & Vanderhye P.C.

(57) ABSTRACT

Compounds able to chelate paramagnetic metal ions and the use thereof as contrast agents in the technique known as "Magnetic Resonance Imaging" (M.R.I.).

13 Claims, No Drawings

BILE ACIDS CONJUGATES WITH METAL ION CHELATES AND THE USE THEREOF

This application is the U.S. national phase of international application PCT/EP01/01971 filed 21 Feb. 2001 which designated the U.S.

The present invention relates to novel compounds able to chelate paramagnetic metal ions and to the use thereof as contrast agents in the technique known as "Magnetic Resonance Imaging" (M.R.I.). In particular, the present invention relates to compounds resulting from the conjugation of a carrier consisting of a bile acid residue with molecules endowed with a chelating capacity, as well as their complex chelates with bi- and trivalent paramagnetic metal ions, the salts thereof and the use thereof as contrast agents for M.R.I.

Patent literature reports a number of patents and patent applications concerning chelates of straight and cyclic polyaminopolycarboxylic ligands with paramagnetic metals as contrast agents for M.R.I. Some of these compounds are already in clinical use (Gd-DTPA, N-methylglucamine salt of the gadolinium complex with diethylenetriaminopentaacetic acid, MAGNEVIST®, Schering; Gd-DOTA, N-methylglucamine salt of the gadolinium/1,4,7,10-tetraazacyclododecane-1,4,7,10-tetraacetic acid complex, DOTAREM®, Guerbet; Gd-HPDO3A, gadolinium complex with 10-(2-hydroxypropyl)-1,4,7,10-tetraazacyclodo-decane-1,4,7-triacetic acid, PROHANCE®, BRACCO). These contrast agents are designed for a wholly general use, as they are mainly distributed in the extracellular spaces after administration.

On the contrary, a contrast agent capable of providing diagnostically useful information even in case of small lesions such as liver tissue metastasis, should selectively accumulate in the intracellular spaces of the parenchyma of said organ. Intracellular hepatobiliary agents are capable of entering hepatocytes through the sinusoid membrane and are mainly excreted through the bile. The lipophilic nature of their chelating units is considered responsible for the preferential uptake by hepatocytes (Lauffer, R. B.; Chem. Rev. 87, 901–927, 1987; Lauffer, R. B. et al.; Magn. Reson. Med. 4, 582–590, 1987).

Cholic acid is one of the bile acids resulting from cholesterol catabolism; it is excreted by hepatocytes into bile (Elliot, W. H.; *Sterols and bile acids*; H. Danielsson and J. Sjövall, Eds.; pp 231–278, Elsevier, N.Y., 1985).

M.R.I. contrast agents comprising a residue of a chelating agent conjugated by a spacing chain to a bile acid residue are disclosed in WO95/01958. Said agents are stated to be particularly useful in the imaging of liver and bile ducts.

It has also been found that the bile acid residue makes the chelanting agents including it capable of interacting with plasma proteins thus forming non-covalent bonds with them. Therefore the contrast agents comprising a bile acid residue are also particularly useful in the N.M.R. imaging of the vasal system, as disclosed in Italian patent application MI98A002802, which is herein incorporated by reference in its entirety.

EP 279,307 (Abbott) discloses other polyaminopolycarboxylic chelants, capable of complexing metal ions, conjugated with different substrates, inter alia bile acids, as contrast agents. The only compound disclosed in this patent application is a $^{111}$In complex of a conjugate in which a functionalized derivative of EDTA is linked, through an amido bond, to the carboxylic function of a cholic acid. The possibility of chelating paramagnetic metal ions for use in M.R.I. is not referred to in any way.

Betebenner David A. et al. in Bioconjugate Chem. 2; 117–123, 1991 disclose the preparation and characterization of an EDTA derivative conjugated with a cholic acid and of the corresponding chelated complex with [111]In. The conjugation takes place through the terminal amino group of a functional derivative of EDTA with a cholic acid ester, by means of a reaction already used for linking chelating units to proteins (Westerberg, D. A. et al., J. Med. Chem. 32, 236–243, 1989; Brechbiel, M. W. Et al., Inorg. Chem. 25, 2772–2781, 1986). Biodistribution and scintigraphic imaging studies carried out with this compound show that, after uptake by the liver, it rapidly passes into the intestine.

All known agents comprising the residue of a bile acid are characterized by the presence of a single chelating unit and, therefore, of a single metal ion coordinated per each molecule of the agent itself.

The present invention relates to compounds capable of chelating at least two metal ions. Said compounds are obtained by conjugation of a carrier consisting of a bile acid residue with two chelating molecules, said conjugation taking place through a central reactive polyfunctional substrate or central synton. In particular, the bonds between the central syntons of the invention and the chelating units are obtained by means of functional residues suitably selected so that said chelating units can keep unaltered their capability to coordinate the metal ion and the stability of the resulting chelates does not decrease.

More particularly, the present invention relates to compounds of general formula (I)

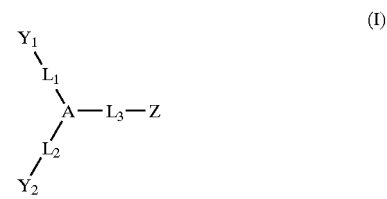

wherein:

A is a polyfunctional reactive substrate containing at least three functional groups deriving from any polyvalent organic residue which can be aliphatic with open chain, optionally branched, or alicyclic, or heterocyclic containing N, O and/or S, or aromatic or heteroaromatic;

Z is a bile acid residue;

$Y_1$ and $Y_2$, which can be the same or different, are the residue of a chelating agent of the bi-trivalent metal ions having atomic numbers ranging between 20 and 31, 39, 42, 43, 44, 49, and between 57 and 83;

$L_1$, $L_2$ and $L_3$, which can be the same or different, are a single bond between the functional groups Y1and A, Y2 and A and/or Z and A, or a spacer comprising at most 20 carbon atoms.

Bile acid herein means all bile acids obtained by bioconversion or synthetic modification of cholesterol, particularly cholic, deoxycholic, chenodeoxycholic, ursodeoxycholic, lithocholic acids and the derivatives thereof, including those with taurine and glycine. Said residues are linked to the $L_3$ group through covalent bonds involving the hydroxy group, optionally converted to an amino group, at the 3-position or the carboxy group at the 24-position of the cholane skeleton.

Preferred compounds are those in which $L_1$ and $L_2$, which can be the same or different, are a spacer chain of formula (II)

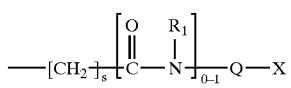

wherein:
Q is a $C_1$–$C_8$ alkyl chain optionally substituted with 1 to 3 OH groups;
s is an integer 0 to 5;
$R_1$ is an H atom, or a $C_1$–$C_5$ alkyl group;
X is

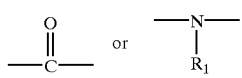

$L_3$ is a group of formula (III)

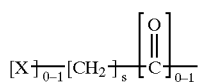

in which: X and s have the above defined meanings (with the proviso that when s is different from 0 then CO and X are present).

Particularly preferred are the compounds in which $L_1$ and $L_2$ are selected from those of formula (IV), (V), (VI)

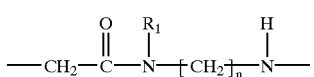

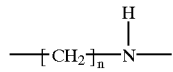

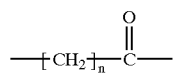

$L_3$ is a single bond between the Z and A functional groups or a group

in which:
n is an integer 1 to 8, and
$R_1$ has the above defined meanings.

The invention also relates to the complex chelates of said compounds of formula (I) with the bi- and trivalent ions of the metal elements having atomic numbers ranging between 20 and 31, 39, 42, 43, 44, 49, and between 57 and 83, as well as the salts thereof with physiologically compatible organic bases selected from primary, secondary, tertiary amines or basic amino acids, or with inorganic bases the cations of which are sodium, potassium, magnesium, calcium or mixtures thereof, or with anions of physiologically acceptable organic acids selected, for example, from acetate, succinate, citrate, fumarate, maleate, oxalate, or with anions of inorganic acids such as ions of halo acids, i.e. chlorides, bromides, iodides.

The invention also relates to the preparation of the compounds of general formula (I) as well as the complex salts thereof and the use thereof for the preparation of pharmaceutical formulations for the diagnostic use, in particular for M.R.I. contrast formulations.

Furthermore, the compounds of the invention can optionally be chemically conjugated with suitable macromolecules or englobated in suitable carriers.

Preferred compounds are those in which Z is a residue deriving from the following bile acids or derivatives thereof with taurine and glycine:

Bile acids

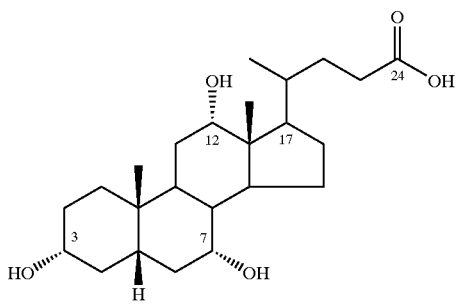

Colic acid

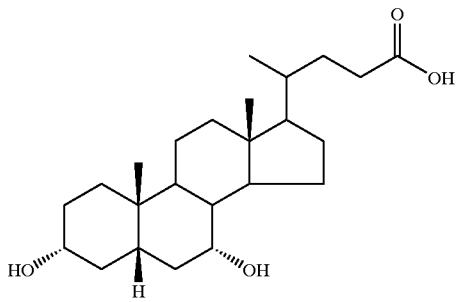

Chenodeoxycholic acid

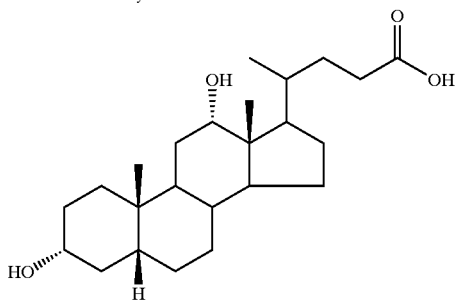

Deoxycholic acid

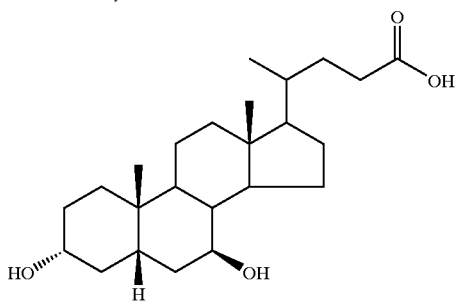

Ursodeoxycholic acid

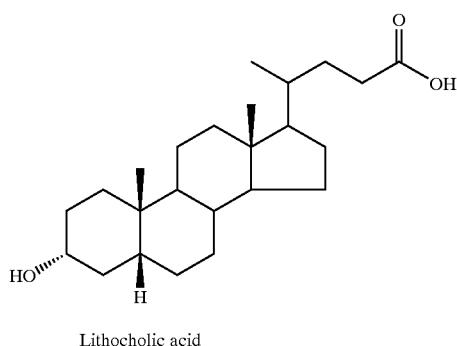

Lithocholic acid

A is a polyfunctional reactive substrate having preferably amino and/or carboxy groups. Preferred examples of substrates A are reported in Table 1.

TABLE 1

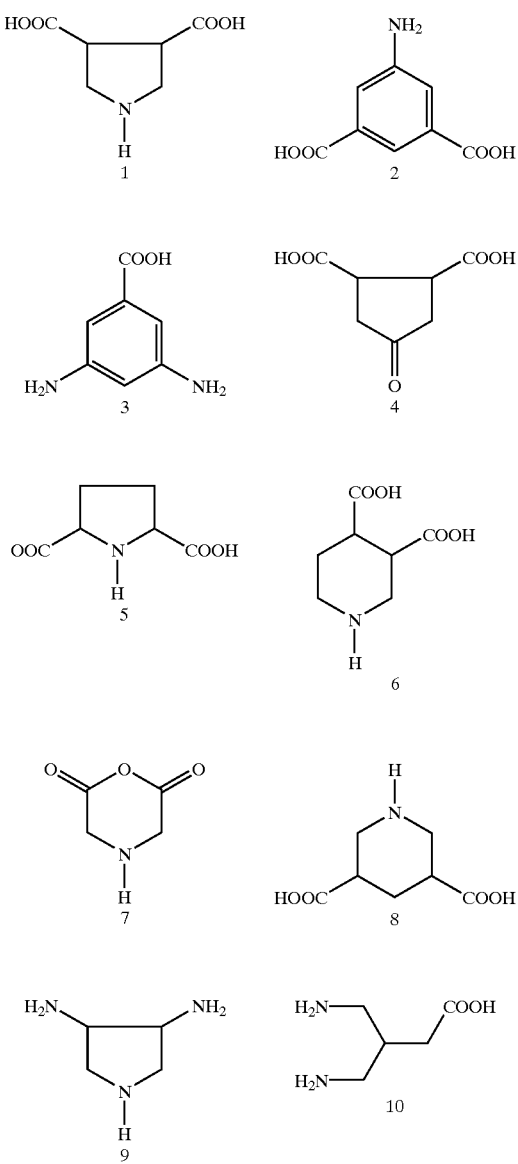

TABLE 1-continued

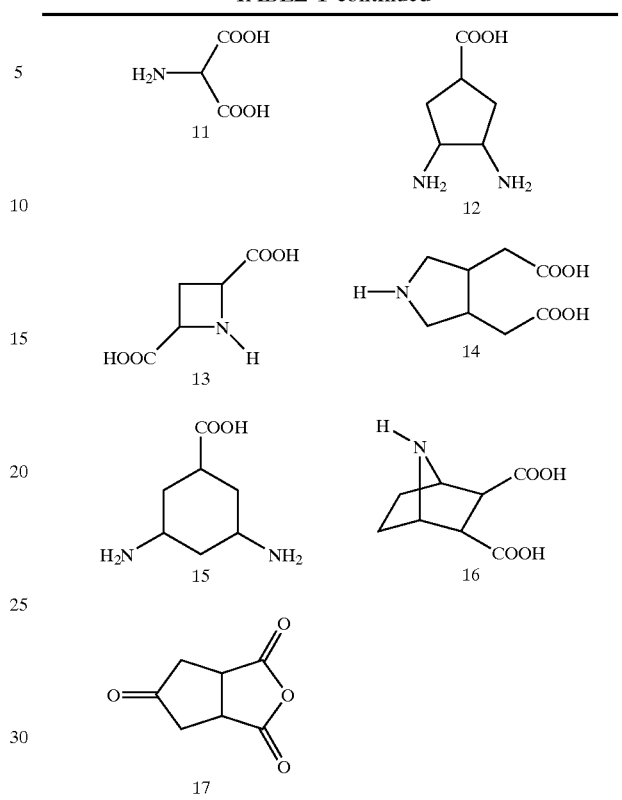

The compounds 1–17 can be used as such or as amino- or carboxy-protected or activated derivatives.

$Y_1$ and $Y_2$ are preferably the residues of two polyaminopolycarboxylic ligands, either in the form of acids or of derivatives thereof. More particularly, $Y_1$ and $Y_2$ are preferably residues of diethylenetriaminopentaacetic (DTPA), 1,4,7,10-tetraazacyclododecane-1,4,7,10-tetracetic (DOTA), 10-(2-hydroxypropyl)-1,4,7,10-tetraazacyclododecane-1,4,7-triacetic (HPDO3A), 4-carboxy-5,8,11-tris(carboxymethyl)-1-phenyl-2-oxa-5,8,11-triazatridecan-13-oic (BOPTA) acids, or of N-[2-[bis(carboxymethyl)amino]-3-(4-ethoxyphenyl)propyl]-N-[2-[bis(carboxymethyl)amino]ethyl]glycine (EOB-DTPA) and N,N-bis[2-[(carboxymethyl)[(methylcarbamoyl)methyl]amino]-ethyl]glycine (DTPA-BMA).

Particularly preferred are the compounds in which Z is a cholic acid residue, A is a polyfunctional substrate selected from those of formulae 1, 2, 3, 4 and 17 and $Y_1$ and $Y_2$, which can be the same or different, are selected from residues shown in the following Table 2:

TABLE 2

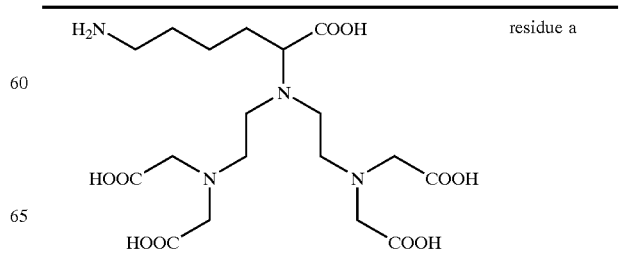

residue a

TABLE 2-continued

| | |
|---|---|
| (structure with HOOC groups and branched N) | residue b |
| (structure with H2N and COOH) | residue c |
| (macrocyclic structure with OH and NH2) | residue d |
| (macrocyclic structure with CONH-NH2) | residue e |
| (structure with H2N and HOOC) | residue f |

Particularly preferred are the following compounds:

[3α[3(S),4(S)],5β,12α]-3-[[[trans-3,4-bis[[[5-[bis[2-[bis(carboxymethyl)-amino]ethyl]amino]-5-carboxypentyl]amino]carbonyl]-1-pyrrolidinyl]carbonyl]oxy]-12-hydroxycholan-24-oic acid;

[3α[3(S),4(S)],5β,12α]-3-[[[trans-3,4-bis[[[2-[bis[2-[bis(carboxymethyl)amino]ethyl]amino]-2-carboxyethyl]amino]carbonyl]-1-pyrrolidinyl]carbonyl]oxy]-12-hydroxycholan-24-oic acid;

(3α,5β,12α)-3-[[[trans-3,4-bis[[[2-[[[4,7,10-tris(carboxymethyl)-1,4,7,10-tetraazacyclododec-1-yl]acetyl]amino]ethyl]amino]carbonyl]-1-pyrrolidinyl]carbonyl]oxy]-12-hydroxycholan-24-oic acid;

[3α[3(S),4(S)],5β,12α]-3-[[[trans-3,4-bis[[[5-[[2-[bis(carboxymethyl)-amino]ethyl](carboxymethyl)amino]-5-carboxypentyl]amino]carbonyl]-1-pyrrolidinyl]carbonyl]oxy]-12-hydroxycholan-24-oic acid;

[3α[1(S),2(S)],5β,7α12α]-3-[[[[cis-1,2-bis[[[5-[bis[2-[bis(carboxymethyl)-amino]ethyl]amino]-5-carboxypentyl]amino]carbonyl]-4-cyclopentyl]amino]-carbonyl]oxy]-7,12-dihydroxycholan-24-oic acid;

[3α[1(S)],5β,7α,12α]-3-[[[[cis-1-[[[5-[bis[2-[bis(carboxymethyl)amino]ethyl]-amino]-5-carboxypentyl]amino]carbonyl]-2-[[[2-[[[4,7,10-tris(carboxymethyl)-1,4,7,10-tetraazacyclododec-1-yl]acetyl]amino]ethyl]amino]carbonyl]-4-cyclopentyl]amino]carbonyl]oxy]-7,12-dihydroxycholan-24-oic acid;

[3β[3(S),5(S)],5β,7α,12α]-3-[[[3,5-bis[[4-[bis[2-[bis(carboxymethyl)amino]-ethyl]amino]-4-carboxy-1-oxobutyl]amino]phenyl]carbonyl]amino]-7,12-dihydroxy-cholan-24-oic acid;

as well as the chelates and the physiologically compatible salts thereof.

Suitable ions for forming complex salts with the chelating agents of general formula (I) are bivalent or trivalent ions of the elements having atomic numbers ranging between 20 and 31, 39, 42, 43, 44, 49, between 57 and 83; particularly preferred are $Fe^{(2+)}$, $Fe^{(3+)}$, $Cu^{(2+)}$, $Cr^{(3+)}$, $Gd^{(3+)}$, $Eu^{(3+)}$, $Dy^{(3+)}$, $La^{(3+)}$, $Yb^{(3+)}$, or $Mn^{(2+)}$, or also radioisotopes such as $^{51}Cr$, $^{67}Ga$, $^{68}Ga$, $^{111}In$, $^{99m}Tc$, $^{140}La$, $^{175}Yb$, $^{153}Sm$, $^{166}Ho$, $^{90}Y$, $^{149}Pm$, $^{177}Lu$, $^{47}Sc$, $^{142}Pr$, $^{159}Gd$, $^{212}Bi$.

The compounds of the present invention have shown good tolerability as well as water solubility.

The improvement of the M.R.I. imaging that the radiologist can observe, namely an increase in the contrast between healthy and affected tissues, is certainly an aid for diagnosis. Said improvement is generally obtained by administering the patient with suitable exogenous compounds, such as the suitably complexed paramagnetic metal ions, capable of significantly changing the relaxivity of the water protons of the tissue they are in contact with, when said protons are subjected to an outer magnetic field.

The change induced by the presence of two paramagnetic metal ions per molecule of the administered agent, characteristic of the compounds of the invention, is significantly enhanced thereby obtaining a contrast between healthy and affected tissue which is already diagnostically useful at lower dosages of contrast agents.

An advantage of the complex chelates of the invention is therefore that they can be used in low-dosage diagnostic formulations capable of providing good-quality images while remarkably decreasing the toxicity and the discomfort unavoidably involved by the administration of an exogenous substance, such as a contrast agent.

The compounds of the invention can therefore be advantageously administered at doses ranging from 0.005 to 1.0 mmol/kg, and preferably from 0.01 to 0.1 mmol/kg.

Thanks to the presence in the molecule of a carrier such as the bile acid residue, the agents of the invention can interact with plasma proteins and form non-covalent bonds therewith. This property thus provides high relaxivity in the serum and such long permanency in blood as to make them particularly suitable for M.R.I. imaging of the vascular system.

It has been surprisingly found that, in addition to increasing the number of the paramagnetic metal ions present, which involves advantages in terms of relaxivity and signal intensity, the introduction of a second chelating unit in the compounds of the invention induces a remarkable change in the excretion mechanism thereof. The compounds of the invention, in fact, are surprisingly almost completely excreted thorough the renal route, by glomerular filtration. The experimental results of the pharmacokinetic screening in rats indicate that during a period of 0 to 480 min, 36.2% of the administered compound was eliminated with urine and only 0.175% of the injected dose with bile. A detailed description of the experimental conditions as well as of the obtained results is included, as a non-limiting example, in the experimental section.

The compounds of the invention, therefore, while maintaining unaffected the properties deriving from the presence of the bile acid residue, do not enter liver intracellular spaces and are excreted through the bile only to a very limited extent, contrary to the compounds of the prior art containing one chelant residue only.

This involves, on the one hand, an unexpected improvement in terms of toxicity and, on the other hand, total absence of metabolization by hepatocytes.

From still another point of view, the agents of the invention have remarkably increased half-life in blood, as they are captured and englobated by the hepatocytes only to a very low extent. This further unexpected property, as well as the increased relaxivity in serum, contribute to make the agents of the present invention particularly suitable for the imaging of the vascular system in general, and particularly of coronaries, even at the lows dosages used.

The compounds of general formula (I) can be prepared with synthetic methods usually employed in industrial technique.

In particular, the preparation of compounds in which the two chelating units are the same is performed according to a synthetic process similar to that illustrated in the following Scheme, representing the synthesis of the compound of Example 1, as detailed in the experimental section.

Scheme

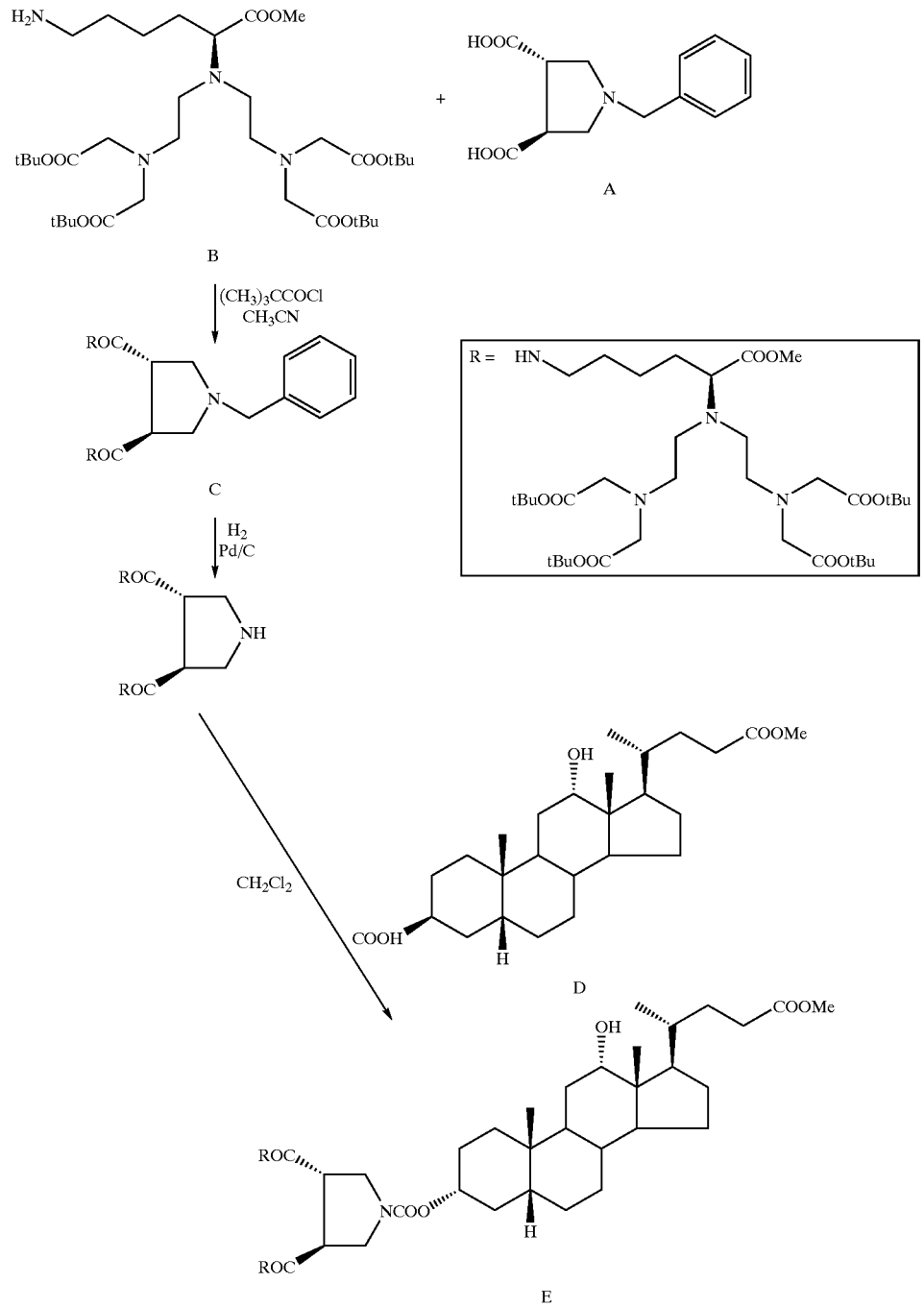

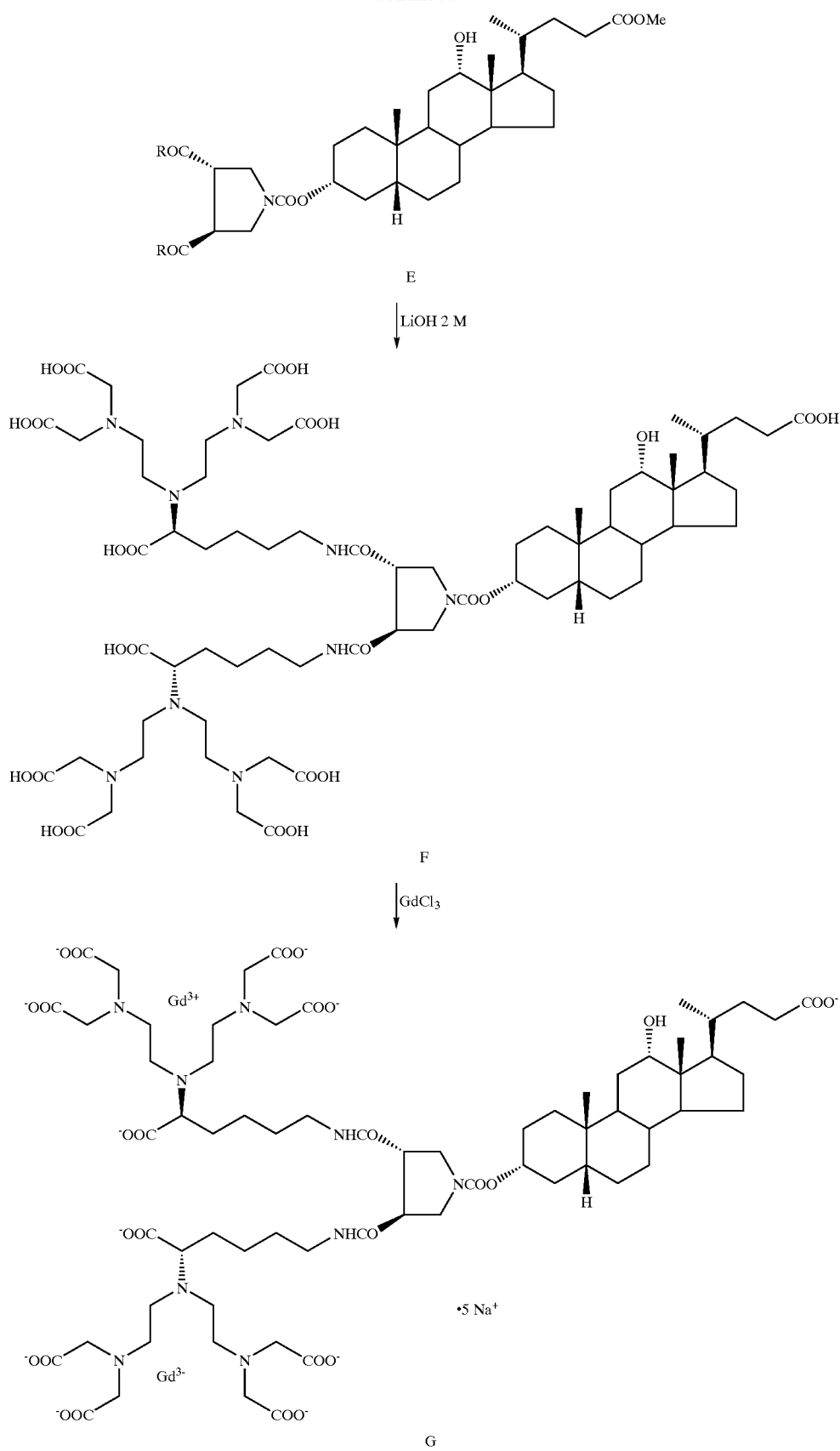

Briefly, the synthetic process of the scheme comprises the following steps:
1) synthesis of the central polyfunctional residue A in a suitable form, in which the functional groups can independently be suitably protected or activated;
2) synthesis of the suitably functionalized chelant residue B, i.e. of a chelating agent capable of stably coordinating the metal ions as well as of covalently binding to the central polyfunctional residue through a suitable functional group;
3) linking between central polyfunctional residue and chelant residues and isolation of intermediate C;
4) synthesis of a suitably functionalized bile acid D capable of stably binding to the central polyfunctional residue through a suitable functional group;
5) optional cleavage and/or activation of the third functional residue A, linking between the resulting compound and D and isolation of E;
6) cleavage of any protective groups and isolation of polyacid F;
7) complexation of the metal ions and isolation of the chelated complex G.

When the two chelating units of the compounds are different, the contrast agents of the invention can be prepared by using a similar synthetic process in which intermediate C is prepared by reacting the suitable polyfunctional residue A with a first chelant residue B1, subsequent activation of a second functional group A and linking between it and the second chelant residue B2.

Briefly, said process comprises the following synthetic steps:
1) synthesis of the central polyfunctional residue A in a suitable form, in which the functional groups can independently be suitably protected or activated;
2) synthesis of the two suitably functionalized chelant residues B1 and B2, i.e. of two chelant units capable of stably coordinating the metal ions as well as of covalently binding to the central polyfunctional residue through a suitable functional group;
3) linking between polyfunctional residue and a first chelant residue B1; optional cleavage and/or activation of a second functional residue A, linking between it and a chelating unit B2 and isolation of intermediate C;
4) synthesis of a suitably functionalized bile acid D, capable of stably binding to the central polyfunctional residue through a suitable functional group;
5) optional cleavage and/or activation of the third functional residue A, linking between the resulting compound and D and isolation of E;
6) cleavage of any protective groups and isolation of polyacid F;
7) complexation of the metal ions and isolation of the chelated complex G.

Said compounds, or the suitable precursors and/or functional derivatives thereof, can be easily obtained according to the known synthetic techniques.

By way of example, compound 2 is commercially available, derivatives of compound 7 in which the amino groups are suitably protected can be prepared as described in J. Am. Chem. Soc. 1996, 118, 2567 or in Polymer 1982, 23, 771; compound 5 as described in Tetrahedron Lett. 1993, 34, 4989; compound 4 dimethyl ester as described in J. Org. Chem. 1989, 54, 5115; compound 1 dimethyl ester with the amino residue suitably protected as benzyl derivative, as described in Bull. Soc. Chim. Fr. 1988, 579; compound 3 derivative in which the amino functions are appropriately protected, as described in Chem. Commun. 1998, 1629; compounds 6 and 8 dimethyl esters in which the amino functions are suitably protected, as described in J. Chem. Soc. Perkin trans. I 1991, 409 and Tetrahedron Lett. 1994, 35, 4515 respectively; compound 13 dimethyl ester as described in J. Med. Chem. 1990, 33, 1561; anhydride 17 as described in Chem. Pharm. Bull. 1984, 32, 805.

The residues of Table 2 can be prepared using known techniques. The residues a, b and c can, for example, be prepared analogously to what described in Bioconjugate Chem. 1999, 10, 137; the preparation of the residue d is described in WO 9601655, that of the residue e in WO 9528967, that of f is described in the experimental section, Example 4.

Preferred bile acid functional derivatives for the preparation of the compounds of the invention are, for example, the 3β-amino derivatives thereof, obtained starting from corresponding 3α-hydroxyls following the synthetic process described in Synth. Commun. 1998, 28, 109.

Also preferred are chloroorthoformates obtained from the corresponding 3α-hydroxyls according to the synthetic process described in J. Am. Chem. Soc. 1997, 117, 640.

Both cited derivatives can be used in the linking reactions directly, or they can be further modified by reacting the respective functional groups with suitable bifunctional spacers.

A list of particularly preferred bile acid functional derivatives is reported hereinbelow. For many compounds, the list also reports a bibliographic reference concerning the preparation thereof.

Bile Acid Functional Derivatives

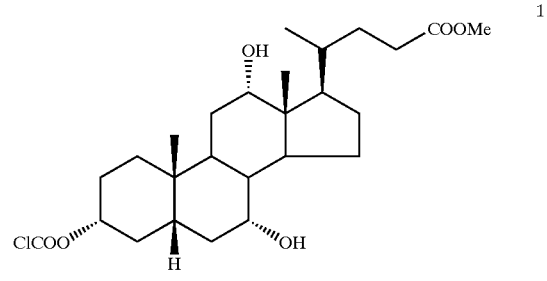

J. Am. Chem. Soc. 1997, 117, 640

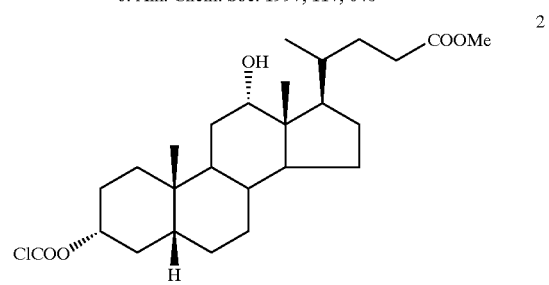

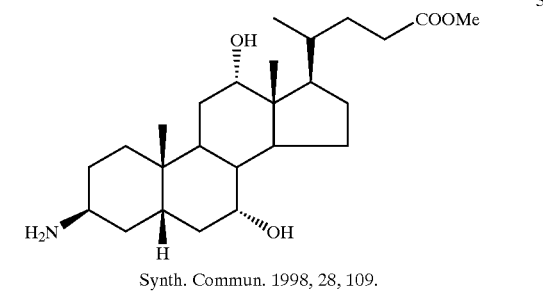

Synth. Commun. 1998, 28, 109.

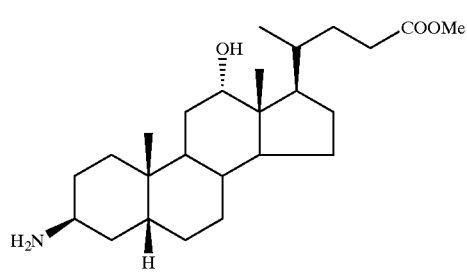

Synth. Commun. 1998, 28, 109.

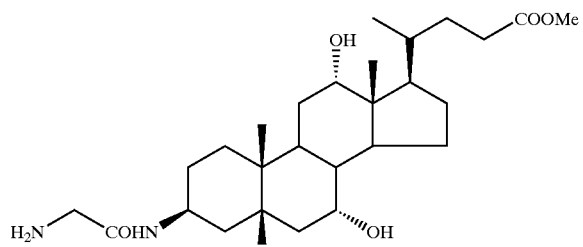

WO 9532741

The linking between polyfunctional central nucleus and chelant residue can take place, for instance, between a suitably functionalized amino group present on the chelant and a carboxylic residue present on the polyfunctional central residue or, vice versa, between a carboxylic residue of the suitable ligand functional derivative and an amino residue of the central polyfunctional residue to form an amide in both cases.

The linking between the central polyfunctional residue and the bile acid residue can take place by formation of an amido bond, for example between the acid group at the 24-position of the bile residue and an amino group present in the central polyfunctional synton, according to a procedure widely described and used in the preparation of, for example, peptides (Tetrahedron, 32, 2211, 1976).

Alternatively, the amido bond can be formed between the amino group of a bile acid 3β-amino derivative and a carboxylic group of the central polyfunctional residue, or between the chlorocarbonyl residue of the bile acid chloroformate and an amino group of the central polyfunctional residue.

Said linking may optionally be preceded by cleavage and/or activation of the functional group of the central unit involved in the reaction.

Amino functional groups are usually protected by transformation into the corresponding benzyl, carbobenzyloxy (Cbz) or tert-butyloxycarbonyl (BOC) derivatives. In the first two cases, for example, the cleavage reaction can take place by hydrogenation of the benzyl or Cbz derivatives, in the presence of a suitable metal catalyst, for example Pd/C. In the third case, cleavage can be obtained in acidic conditions, for example with CF3COOH.

The carboxylic residues are usually protected by transformation into suitable esters. The subsequent deprotection of carboxylic functions of the two chelant units can be obtained by hydrolysis of the protective ester groups, for example with LiOH, CF3COOH or iodotrimethylsilane in a suitable organic solvent, such as dioxane, $CH_2Cl_2$ or $CH_3CN$ or an alcohol, such as i.PrOH.

The compounds of the invention have a wide range of applications, since they can be administered through the intravasal (for instance intravenous, intraarterial, intracoronaric, intraventricular routes, and so on), intrathecal, intraperitoneal, intralymphatic and intracavital routes. The compounds are also suitable for the oral or enteral administration, and therefore, for the imaging of the gastrointestinal tract.

For the parenteral administration, the compounds of the invention are preferably formulated as sterile solution or aqueous suspension, with pH preferably ranging from 6.0 to 8.5. Said aqueous solutions or suspensions can be administered in concentrations ranging from 0.002 to 1.0 molar. The resulting formulations can be lyophilized and supplied as such, to be reconstituted prior to use.

For the gastrointestinal use or for injection to body cavities, these agents can be formulated as a solution or suspension containing suitable additives in order to, for example, control viscosity.

For the oral administration they can be formulated according to preparation methods routinely used in the pharmaceutical technique or as coated formulations to gain extra protection from the acid pH of stomach, inhibiting the release of the chelated metal ion, which usually occurs at typical pH values of gastric juices.

Other excipients, such as sweeteners and/or flavoring agents, can be also added according to known techniques of pharmaceutical formulation.

The solutions or suspensions of the compounds of this invention can also be formulated as aerosol to be used in aerosol-bronchography and instillation.

As far as diagnostic imaging is concerned, the chelates of this invention can also be used as radiopharmaceuticals in nuclear medicine both in the diagnostic and therapeutic field. However, in this case the metal ion which is chelated is a radioisotope, such as $^{51}Cr$, $^{67}Ga$, $^{68}Ga$, $^{111}In$, $^{99m}Tc$, $^{140}La$, $^{175}Yb$, $^{153}Sm$, $^{166}Ho$, $^{90}Y$, $^{149}Pm$, $^{177}Lu$, $^{47}Sc$, $^{142}Pr$, $^{159}Gd$, $^{212}Bi$.

Preferred cations of inorganic bases which can be suitably used to salify complex chelates of this invention particularly comprise ions of alkali or alkaline-earth metals such as potassium, sodium, calcium, magnesium and the mixtures thereof.

Preferred cations of organic bases suitable for the above mentioned aim, comprise, among others, those of primary, secondary and tertiary amines such as ethanolamine, diethanolamine, morpholine, glucamine, N-methylglucamine, N,N-dimethylglucamine.

Preferred anions of inorganic acids which can be suitably used for the salification of complex chelates of this invention particularly comprise anions of the hydrohalo acids such as chlorides, bromides, iodides or other anions such as sulfate.

Preferred anions of organic acids suitable for the above mentioned aim comprise those of acids routinely used in pharmaceutical technique for the salification of basic substances, such as acetate, succinate, citrate, maleate and fumarate.

Preferred cations and anions of amino acids comprise, for example, those of taurine, glycine, lysine, arginine, ornithine or of aspartic and glutamic acids.

The compounds of the invention can be encapsulated or in liposomes or form the constituents of their chemical structure and used as uni- or multilamellar vesicles.

The compounds of the invention can also be conjugated with macromolecules or englobated into or combined with suitable carriers.

In the following, a non-limiting list of preferred compounds of the invention is reported.

COMPOUND 1 (EXAMPLE 1)
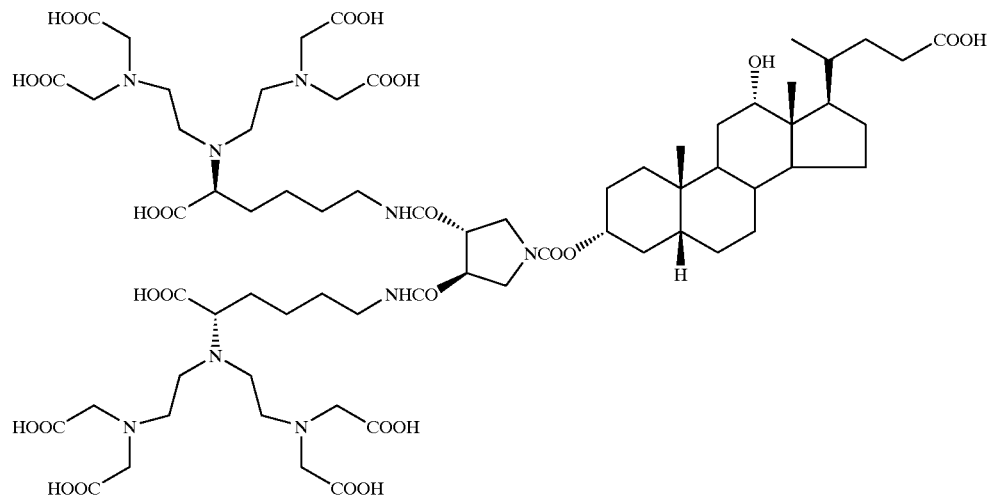
COMPOUND 2 (EXAMPLE 2)
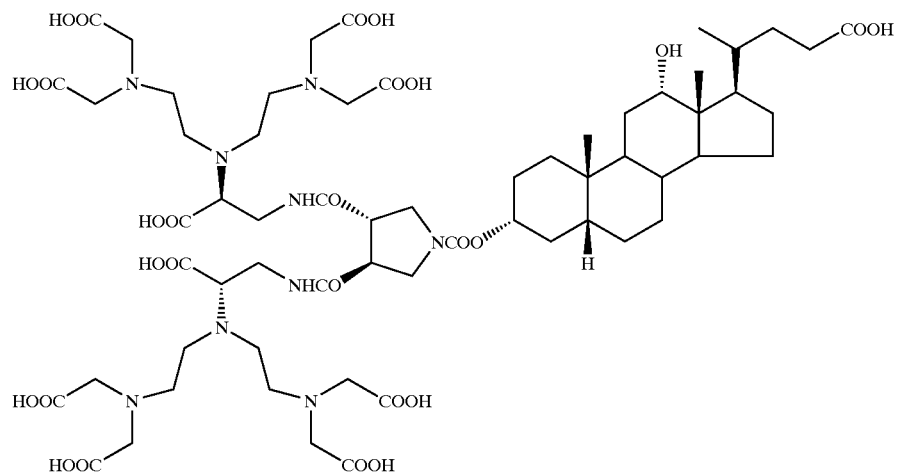
COMPOUND 3 (EXAMPLE 3)
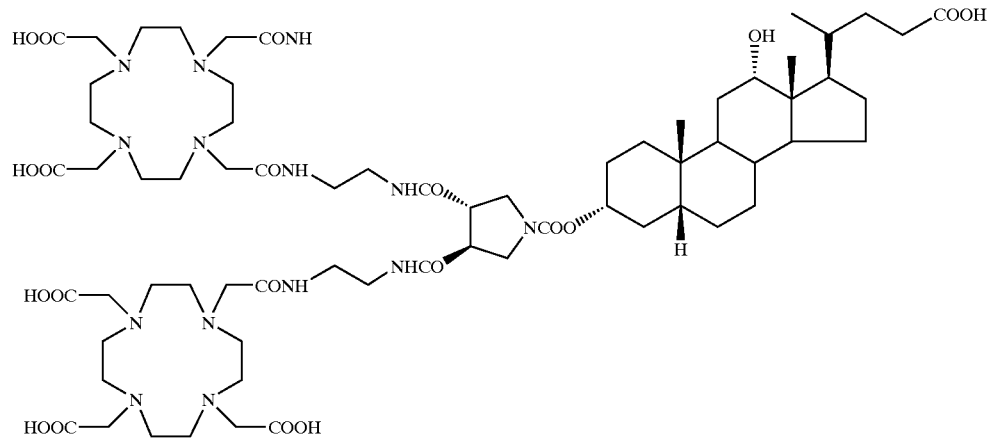

COMPOUND 4 (EXAMPLE 4)
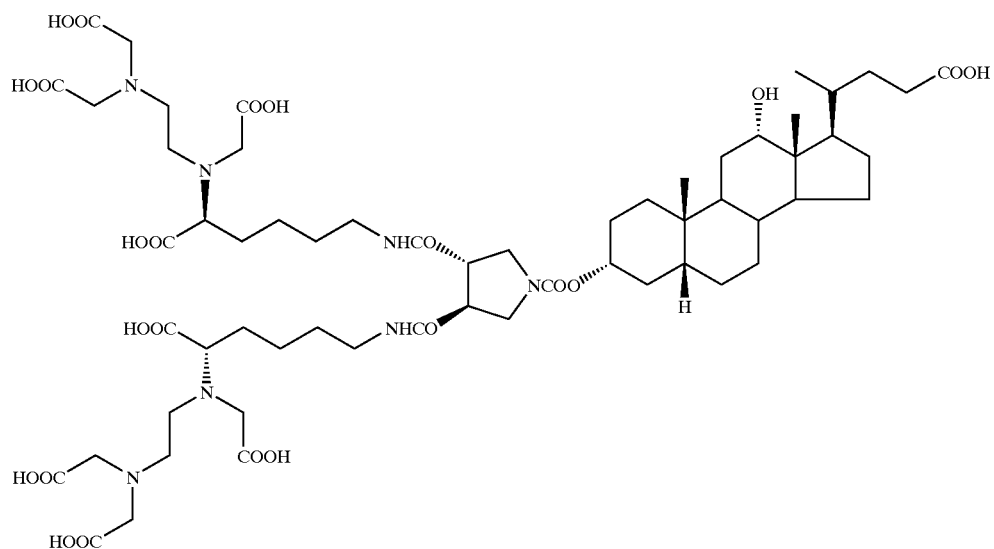
COMPOUND 5 (EXAMPLE 5)
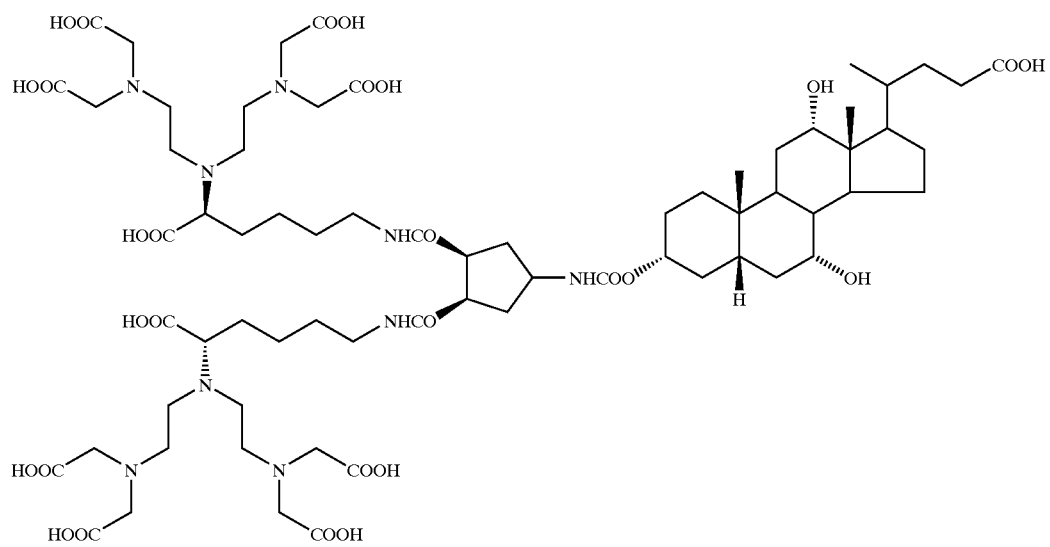
COMPOUND 6 (EXAMPLE 6)
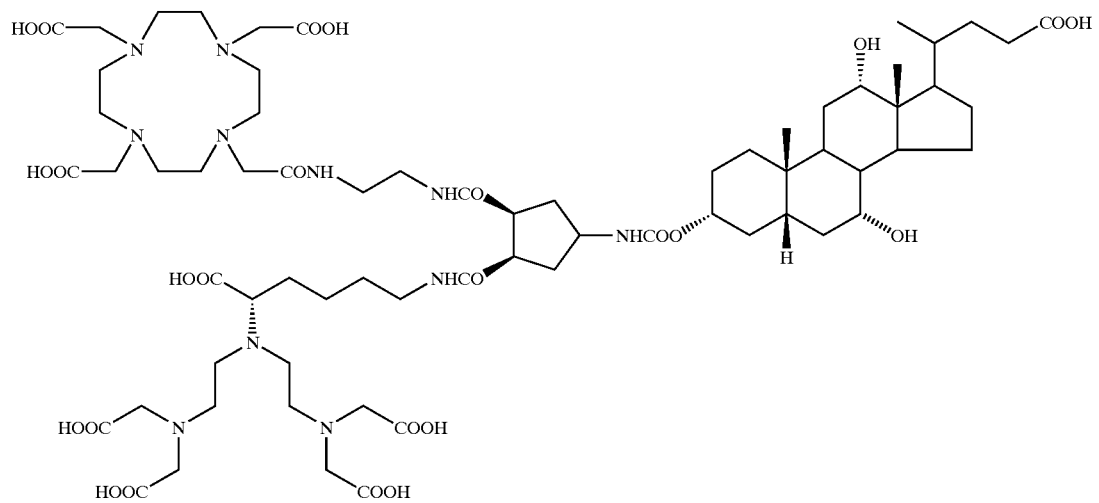

COMPOUND 7 (EXAMPLE 7)

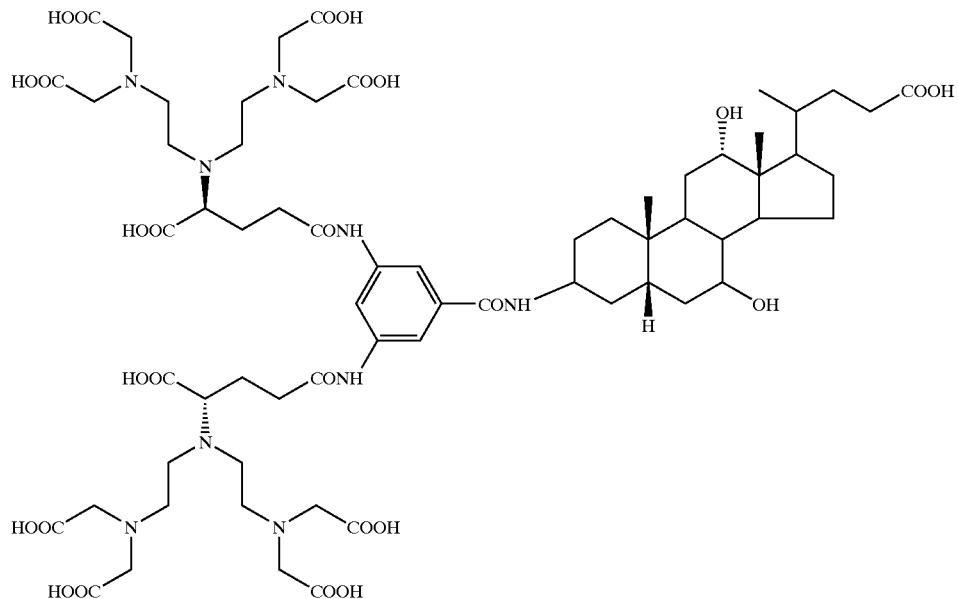

EXPERIMENTAL SECTION

EXAMPLE 1

Gadolinium complex of [3α[3(S),4(S)],5β,12α]-3-[[[trans-3,4-bis[[[5-[bis[2-[bis(carboxymethyl)amino]ethyl]amino]-5-carboxypentyl]amino]carbonyl]-1-pyrrolidinyl]carbonyl]oxy]-12-hydroxycholan-24-oic acid salified with sodium (1:5)

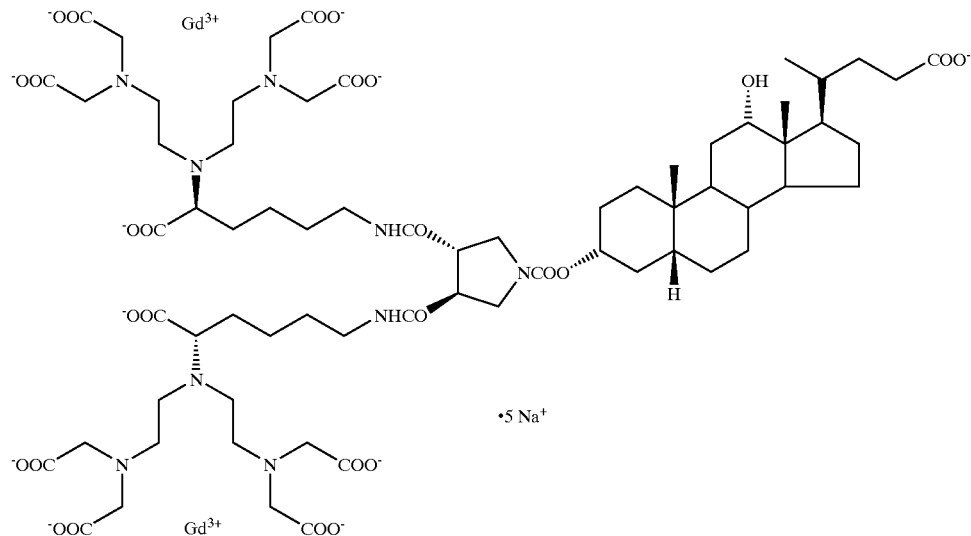

a) trans-1-(phenylmethyl3,4-pyrrolidinedicarboxylic acid.

Trans-1-(phenylmethyl)-3,4-pyrrolidinedicarboxylic acid dimethyl ester (13.4 g; 48.3 mmol) (prepared as described in Bull. Soc. Chim. Fr. 1988, 579) is dissolved in a mixture of EtOH (220 mL) and $H_2O$ (35 mL) and saponified with 1N NaOH (96.4 mL). The solution is then concentrated and the residue taken up into 100 mL of $H_2O$. The solution is acidified to pH 1.8 with 6N HCl to precipitate the acid which is isolated as a white solid (10 g; 40.11 mmol).

Yield: 83%
M.p.: 140–145° C.
HPLC assay: 99.5% (in % area)
Elemental analysis:
% calc.: C 62.24; H 6.07; N 5.62.
% found: C 63.77; H 6.15; N 5.63.

$^1$H-NMR, $^{13}$C-NMR, IR and MS spectra are consistent with the indicated structure.

b) $N^2,N^2$-Bis[2-[bis[2-(1,1-dimethylethoxy)-2-oxoethyl]amino]ethyl]-$N^6$-[(phenylmethoxy)carbonyl]-L-lysine methyl ester.

$N^6$-[(phenylmethoxy)carbonyl]-L-lysine methyl ester hydrochloride (10.6 g; 32.2 mmol) (commercial product)

and N-(2-bromoethyl)-N-[2-(1,1-dimethylethoxy)-2-oxoethyl]glycine 1,1-dimethylethyl ester (prepared according to Rapoport, J. Org. Chem. 1993, 58, 1151) (27.2 g; 77.1 mmol) are dissolved in $CH_3CN$ (160 mL). The mixture is then added with buffer phosphate 2M pH 8 (160 mL) and stirred for 2 hours. The phases are then separated, the aqueous layer is replaced with fresh buffer (160 mL) and the mixture is stirred for a further 70 hours. The organic phase is then separated and evaporated, and the residue is taken up into $CH_2Cl_2$ (150 mL). The resulting methylene solution is washed with $H_2O$ and evaporated to a residue to obtain an oil which is purified by silica gel chromatography. The homogeneous fractions are evaporated to obtain the title compound as a yellow oil (18.1 g; 21.7 mmol).

Yield: 67%
HPLC assay: 97.8 (in % area)
TLC: Carrier: silica gel plate 60F 254 Merck
Eluent: n-hexane/AcOEt=1:1.
Detection: 1% $KMnO_4$ in 1M NaOH; Rf=0.58
Elemental analysis:
% calc.: C 61.70; H 8.67; N 6.69;
% found: C 61.85; H 8.74; N 6.34.
Specific rotatory power: $[\alpha]_D^{20}$=−27.05; (c 5.1, $CHCl_3$).
$^1$H-NMR, $^{13}$C-NMR, IR and MS spectra are consistent with the indicated structure.

c) $N^2,N^2$-Bis[2-[bis[2-(1,1-dimethylethoxy)-2-oxoethyl]amino]ethyl]-L-lysine methyl ester A solution of the intermediate from step b) (40 g; 47.5 mmol) in MeOH (700 mL) is added with carbon on Palladium (4 g; 5% Pd). The suspension is stirred at room temperature under hydrogen atmosphere for 4 hours, then filtered through Millipore® HA 0.45 μm filter and the catalyst is washed with MeOH. The solution is evaporated to obtain the desired product as yellow oil (32.5 g; 46.2 mmol).

Yield: 97%
HPLC assay: 99 (in % area)
TLC: Carrier: silica gel plate 60F 254 Merck
Eluent: n-hexane/AcOEt=1:1.
Detection: 1% $KMnO_4$ in 1M NaOH; Rf=0.13
Elemental analysis:
% calc.: C 59.80; H 9.46; N 7.97; $H_2O$
% found: C 57.89; H 9.44; N 7.39; $H_2O$ 0.98.
Specific rotatory power: $[\alpha]_D^{20}$=−28.68; (c 5.0, $CHCl_3$).
$^1$H-NMR, $^{13}$C-NMR, IR and MS spectra are consistent with the indicated structure.

d) $N^6$, $N^{6'}$-[[trans-1-(phenylmethyl)-3,4-pyrrolidinediyl]biscarbonyl]bis[$N^2$, $N^2$-bis[2-[bis[2-(1,1-dimethylethoxy)-2-oxoethyl]amino]ethyl]-L-lysine] dimethyl ester.

A solution of the compound from step a) (4.0 g; 16.0 mmol) in $CH_3CN$ (110 mL), cooled to 0° C. and kept under nitrogen atmosphere, is added with triethylamine (4.9 mL; 35.3 mmol) and then pivaloyl chloride (4.4 mL; 35.3 mmol). After 20 min the resulting mixture is added dropwise with a solution of the compound from step c) (24.8 g; 35.3 mmol) in $CH_3CN$ (90 mL). The mixture is then warmed at room temperature and kept under these conditions for 1 h, then evaporated. The residue is taken up into AcOEt (300 mL), washed with $H_2O$ and concentrated. The resulting crude oil is purified by silica gel chromatography to obtain the title product as yellow oil (17.5 g; 10.9 mmol).

Yield: 68%
HPLC assay: 98.4% (in % area)
TLC: Carrier: silica gel plate 60F 254 Merck
Eluent: n-hexane/AcOEt=1:1.
Detection: 1% $KMnO_4$ in 1M NaOH; Rf=0.24
Elemental analysis:
% calc.: C 61.57; H 8.90; N 7.79;
% found: C 61.58; H 8.99; N 7.48.
$^1$H-NMR, $^{13}$C-NMR, IR and MS spectra are consistent with the indicated structure.

e) $N^6,N^{6'}$-[[trans-3,4-pyrrolidinediyl]biscarbonyl]bis[$N^2N^2$-bis[2-[bis[2-(1,1-dimethylethoxy)-2-oxoethyl]amino]ethyl]-L-lysine] dimethyl ester.

A solution of compound from step d) (21.6 g; 13.4 mmol) in EtOH (250 mL) is added with carbon on palladium (2.2 g; 5% Pd) and the suspension is kept 4 hours under hydrogen atmosphere, with strong stirring. The mixture is then filtered through a Millipore® FH 0.5 μm filter and evaporated to a residue to obtain the reduction product as yellow oil (18.2 g; 11.9 mmol).

Yield: 90%
HPLC assay 99% (in % area)
Elemental analysis:
% calc.: C 59.70; H 9.03; N 8.24;
% found: C 59.12; H 9.38; N 7.72.
$^1$H-NMR, $^{13}$C-NMR, IR and MS spectra are consistent with the indicated structure.

f) (3α,5β,12α)-3-[(chlorocarbonyl)oxy]-12-hydroxycholan-24-oic acid methyl ester.

A solution of 20% phosgene in toluene (100 mL) is dropped into a solution of (3α,5β,12α)-3,12-dihydroxycholan-24-oic acid methyl ester (14.7 g; 36 mmol) (commercial product) in dry $CH_2Cl_2$ at 0° C. and under nitrogen atmosphere. The solution is stirred for 3 h then evaporated to a residue to obtain the desired product as a white solid (15.2 g; 32.4 mmol).

Yield: 90%.
$^1$H-NMR, $^{13}$C-NMR, IR and MS spectra are consistent with the indicated structure.

g) [3α[3(S),4(S)],5β,12α]-3-[[[trans-3,4-bis[[[5-[bis[2-[bis[2-(1,1-dimethyl-ethoxy)-2-oxoethyl]amino]ethyl]amino]-6-methoxy-6-oxohexyl]amino]carbonyl]-1-pyrrolidinyl]carbonyl]oxy]-12-hydroxycholan-24-oic acid methyl ester.

In a solution of the compound from step f) (5.5 g; 11.7 mmol) and N,N-diisopropylethylamine (4.5 mL) in $CH_2Cl_2$ (150 mL) cooled to 0° C., is dropped, under nitrogen, a solution of the compound from step e) (17.8 g; 11.7 mmol) in $CH_2Cl_2$ (50 mL). The resulting mixture is stirred at room temperature for 3 hours, then washed with $H_2O$ and concentrated. The residue is purified by flash chromatography to obtain the title compound as yellow oil (17.0 g; 8.7 mmol).

Yield: 74%
HPLC assay: 94.4% (in % area)
TLC: Carrier: silica gel plate 60F 254 Merck
Eluent: n-hexane/AcOEt=1:1
Detection: 1% $KMnO_4$ in 1M NaOH; Rf=0.29
Elemental analysis:
% calc.: C 62.46; H 9.10; N 6.43;
% found: C 62.15; H 9.16; N 6.32.
$^1$H-NMR, 13C-NMR, IR and MS spectra are consistent with the indicated structure.

h) [3α[3(S),4(S)],5β,12α]-3-[[[trans-3,4-bis[[[5-[bis[2-[bis(carboxymethyl)-amino]ethyl]amino]-5-carboxypentyl]amino]carbonyl]-1-pyrrolidinyl]carbonyl]oxy]-12-hydroxycholan-24-oic acid.

In a solution of the polyester from step g) (14.0 g; 7.1 mmol) in 1,4-dioxane (190 mL) is dropped, at room temperature, a 2M LiOH aqueous solution (190 mL). After 26 hours the solution is concentrated and added with 2M aqueous HCl to final pH 1.8 (175 mL) to precipitate the acid which is filtered, washed with water and dried to obtain the title product as a white solid (8.7 g; 5.9 mmol).

Yield: 83%
M.p.: 210–215° C.

HPLC assay: 98.9% (in % area)
TLC: Carrier: silica gel plate 60F 254 Merck
Eluent: CHCl$_3$/MeOH/aq. NH$_4$OH=5:4:2
Detection: 1% KMnO$_4$ in 1M NaOH; Rf=0.38
Elemental analysis:
% calc.: C 54.74; H 7.33; N 8.57; H$_2$O
% found: C 51.72; H 7.51; N 8.27, H$_2$O 4.96.
Specific rotatory power: $[\alpha]_D^{20}$=+16.17; (c 1; NaOH 1M)
$^1$H-NMR, $^{13}$C-NMR, IR and MS spectra are consistent with the indicated structure.

i) Gadolinium complex of [3α[3(S),4(S)],5β,12α]-3-[[[trans-3,4-bis[[[5-[bis[2-[bis(carboxymethyl)amino]ethyl]amino]-5-carboxypentyl]amino]-carbonyl]-1-pyrrolidinyl]carbonyl]oxy]-12-hydroxycholan-24-oic acid salified with sodium (1:5).

The ligand from step h) is suspended in water and dissolved by addition of NaOH (32 mL). The resulting solution is added with GdCl$_3$ (3.5 g; 9.6 mmol) in H$_2$O (20 mL), keeping pH at 6.5 by addition of 1M NaOH (17.5 mL). The mixture is kept one hour at room temperature then loaded into an Amberlite XAD® 16.00 column eluting with CH$_3$CN/H$_2$O gradient. The fractions containing the product are evaporated to obtain it as a white solid (8.3 g; 4.4 mmol).

Yield: 92%
M.p.: >300° C.
HPLC assay: 100% (in % area)
El. analysis:
% calc.: C 42.60; H 5.12; N 6.67; Gd 16.65; Na 6.09; H$_2$O
% found: C 37.68; H 5.90; N 5.90; Gd 14.67; Na 6.47; H$_2$O 9.90.
Specific rotatory power: $[\alpha]_D^{20}$=−12.32; (c 2; H$_2$O)
IR and MS spectra are consistent with the indicated structure.

EXAMPLE 2

Following the procedure described in example 1, starting from 3-[[(phenylmethoxy)carbonyl]amino]-N-tert-butoxycarbonyl-L-alanine methyl ester (Chem. Pharm. Bull. 1985, 33, 509), the gadolinium complex of [3α[3(S),4(S)], 5β,12α]-3-[[[trans-3,4-bis[[[2-[bis[2-[bis(carboxymethyl)amino]ethyl]-amino]-2-carboxyethyl]-amino]carbonyl]-1-pyrrolidinyl]carbonyl]oxy]-12-hydroxy-cholan-24-oic acid was prepared.

EXAMPLE 3

Following the procedure described in example 1, starting from 1,4,7-tris-[2-(1,1-dimethylethoxy)-2-oxoethyl]-10-[[2-[2-aminoethyl]amino]-2-oxoethyl]-1,4,7,10-tetraazacyclododecane (WO 95/28967, example 2), the gadolinium complex of (3α,5β,12α)-3-[[[trans-3,4-bis[[[2-[[[4,7,10-tris(carboxymethyl)-1,4,7,10-tetraazacyclododec-1-yl]acetyl]amino]ethyl]amino]carbonyl]-1-pyrrolidinyl]carbonyl]oxy]-12-hydroxycholan-24-oic acid was prepared.

EXAMPLE 4

Following the procedure described in example 1, using MnCl$_2$ for the complexation, the manganese complex of [3α[3(S),4(S)],5β,12α]-3-[[[trans-3,4-bis[[[5-[[2-[bis(carboxymethyl)amino]ethyl](carboxymethyl)amino]-5-carboxypentil]amino]carbonyl]-1-pyrrolidinyl]carbonyl]oxy]-12-hydroxycholan-24-oic was prepared.

The chelant unit used in this case is N$^2$-[2-[bis[2-(1,1-dimethylethoxy)-2-oxoethyl]amino]ethyl]-N$^2$-[2-(1,1-dimethylethoxy)-2-oxoethyl]-L-lysine methyl ester, whose synthesis is described in the following:

a) N$^2$-[2-[bis[2-(1,1-dimethylethoxy)-2-oxoethyl]amino]ethyl]-N$^2$-[2-(1,1-dimethylethoxy)-2-oxoethyl]-N$^6$-[(phenylmethoxy)carbonyl]-L-lysine methyl ester.

A solution of N-(2-bromoethyl)-N-[2-(1,1-dimethylethoxy)2-oxoethyl]glycine 1,1-dimethylethyl ester (21.1 g; 60 mmol) in CH$_3$CN (25 mL) is dropped into a mixture of N$^6$-[(phenylmethoxy)carbonyl]-L-lysine methyl ester hydrochloride (20 g; 60.4 mmol) (commercial product) and N,N-diisopropylethylamine (12.6 mL) in CH$_3$CN (250 mL). After 120 h at room temperature, tert-butyl bromoacetate (18.8 g; 101.6 mmol) and N,N-diisopropylethylamine (17.7 mL) are added. The mixture is stirred for a further 24 h, the solvent is then evaporated off and the residue is dissolved in Et$_2$O and filtered. The ether solution is washed with 0.1M aq. HCl, dried and evaporated to a residue which is purified by flash chromatography. The homogeneous fractions are combined to obtain the desired product as brown oil (13 g; 19 mmol).

Yield: 32%

HPLC purity: 91% (in % area)

TLC: Carrier: silica gel plate 60F 254 Merck

Eluent: n-hexane/AcOEt=7:3

Detection: 1% KMnO$_4$ in 1 M NaOH; Rf=0.4

Elemental analysis:

% calc.: C 61.83; H 8.45; N 6.18;

% found: C 61.70; H 8.52; N 5.84.

$^1$H-NMR, $^{13}$C-NMR, IR and MS spectra are consistent with the indicated structure.

b) N$^2$-[2-[bis[2-(1,1-dimethylethoxy)-2-oxoethyl]amino]ethyl]-N$^2$-[2-(1,1-dimethylethoxy)-2-oxoethyl]-L-lysine methyl ester.

A solution of the compound from step a) (12.3 g; 18.1 mmol) in MeOH (120 mL) is added with carbon on Palladium (1.3 g; 5% Pd) and the suspension is kept 3 hours under hydrogen atmosphere, with strong stirring. The mixture is then filtered through a Millipore® FH 0.5 μm filter and evaporated to a residue to obtain the reduction product which is used directly.

EXAMPLE 5

Gadolinium complex of [3α[1(S),2(S)],5β,7α,12α]-3-[[[[cis-1,2-bis[[[5-[bis[2-[bis(carboxymethyl)amino]ethyl]amino]-5carboxypentyl]amino]-carbonyl]-4-cyclopentyl]-amino]carbonyl]oxy]-7,12-dihydroxycholan-24-oic acid salified with sodium (1:5)

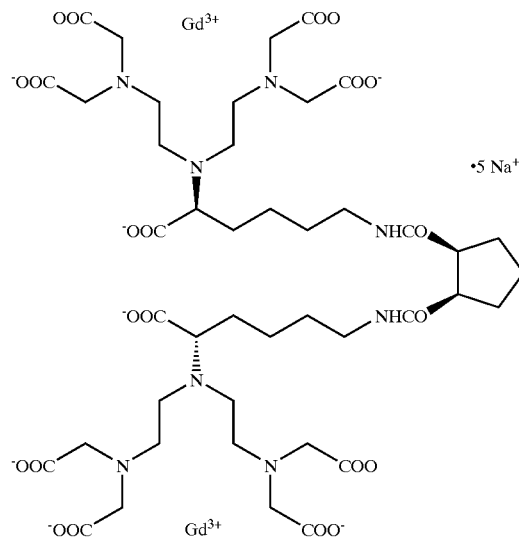
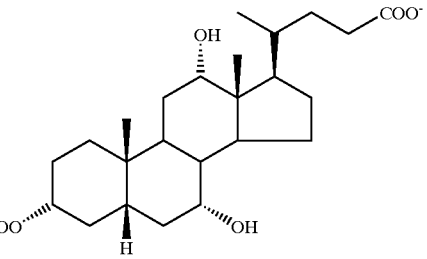

a) N⁶, N⁶'-[(Cis-4-oxo-1,2-cyclopentanediyl)biscarbonyl] bis[N²,N²-bis[2-[bis[2-(1,1-dimethylethoxy)-2-oxoethyl] amino]ethyl]-L-lysine] ditert-butyl ester.

A suspension of cis-tetrahydro-1H-cyclopenta[c]furan-1, 3,5-trione (1.2 g; 7.8 mmol) (obtained as described in Chem. Pharm. Bull. 1984, 32, 805) in THF (30 mL) kept at 20° C. is added dropwise with a solution of N²,N²-bis[2-[bis[2-(1, 1-dimethylethoxy)-2-oxoethyl]amino]ethyl]-L-lysine tert-butyl ester (5.8 g; 7.8 mmol) (Bioconjugate Chem. 1999, 10, 137) in 20 mL THF. After 1h, the reaction mixture cooled to −5° C. is added with triethylamine (2.17 mL; 15.57 mmol) and isobutylchloroformate (1 mL; 7.8 mmol) (commercial product). The mixture is then warned to 20° C. and, after an hour, N²,N²-bis[2-[bis[2-(1,1-dimethylethoxy)-2-oxoethyl] amino]ethyl]-L-lysine tert-butyl ester (5.8 g; 7.8 mmol) in THF (25 mL) is dropped therein. The solution is kept at 20° C. for a further 18 h then concentrated. The residual oil is taken up into CH₂Cl₂ (75 mL) and H₂O (75 mL). The organic phase is separated, dried and purified by column flash chromatography to obtain the desired product (6 g; 3.7 mmol).

Yield: 47%
TLC: Carrier: silica gel plate 60F 254 Merck
Eluent: n-hexane/AcOEt/2-PrOH=7:2:1
Detection: 1% KMnO₄ in 1M NaOH; Rf=0.29
Elemental analysis:
% calc.: C 61.31; H 9.17; N 6.89;
% found: C 61.02; H 9.04; N 6.83.
¹H-NMR, ¹³C-NMR, IR and MS spectra are consistent with the indicated structure.

b) N⁶, N⁶'-[(cis-4-idroxyimino-1,2-cyclopentanediyl) biscarbonyl]bis[N², N²-bis[2-[bis[2-(1,1-dimethylethoxy)-2-oxoethyl]amino]ethyl]-L-lysine] ditert-butyl ester.

A solution of the compound from step a) (14 g; 8.61 mmol) in H₂O (10 mL) and 2-propanol (150 mL), kept at 20° C., is added with hydroxylamine hydrochloride (2.69 g; 38.7 mmol) and sodium acetate (8.8 g; 64.6 mmol). The mixture is heated to 90° C. for 2 hours, concentrated and the residue is taken up into CHCl₃ (100 mL) and H₂O (100 mL). After separation of the phases, the aqueous solution is extracted with CHCl₃ (200 mL). The combined organic phases are dried and concentrated to obtain the desired product as a white solid (11.8 g; 7.2 mmol).

Yield. 84%.

M.p.: 210–215° C.
HPLC assay: 96.8% (in % area)
TLC: Carrier: silica gel plate 60F 254 Merck
Eluent: CHCl₃/MeOH/Aq. NH₄OH=14:2:0.2
Detection: 1% KMnO₄ in 1M NaOH; Rf=0.29
Elemental analysis:
% calc.: C 60.75; H 9.15; N 7.68; H₂O
% found: C 61.11; H 9.26; N 7.54; H₂00.29
¹H-NMR, ¹³C-NMR, IR and MS spectra are consistent with the indicated structure.

c) N⁶,N⁶'-[(cis-4-amino-1,2-cyclopentanediyl)biscarbonyl] bis[N²,N²-bis[2-[bis[2-(1,1-dimethylethoxy)-2-oxoethyl] amino]ethyl]-L-lysine] ditert-butyl ester.

A solution of the compound from step b) (10 g; 6.1 mmol) in CH₃OH (60 mL) is added with Ni-Raney (1.2 g) and the suspension is kept at 30° C. and 30 atm of hydrogen for 18 h. After cooling to 15° C. the solution is concentrated and purified by flash chromatography to obtain the desired product as oil (7.1 g; 4.4 mmol).

Yield: 72%.
HPLC assay: 97.1% (in % area)
K.F.: <0.1%
TLC: Carrier: silica gel plate 60F 254 Merck
Eluent: CHCl₃/MeOH/aq. NH₄OH=14:2:0.2
Detection: 1% KMnO₄ in 1M NaOH; Rf=0.52.
¹H-NMR, ¹³C-NMR, IR and MS spectra are consistent with the indicated structure.

d) [3α[1(S),2(S)],5β,7α,12α]-3-[[[[cis-1,2-bis[[[5-[bis[2-[bis(carboxymethyl)amino]ethyl]amino]-5-carboxypentyl] amino]carbonyl]-4-cyclopentyl]amino]carbonyl]-oxy]-7, 12-dihydroxycholan-24-oic.

Into a solution of (3α,5β,7α,12α)-3-[(chlorocarbonyl) oxy]-7,12-dihydroxycholan-24-oic acid methyl ester (5 g; 10.3 mmol) (obtained as described in J. Am. Chem. Soc. 1997, 117, 640) and N,N-diisopropylethylamine (5 mL) in CH₂Cl₂ (150 mL), cooled at 0° C., is dropped, under nitrogen, a solution of the compound from step c) (16.8 g; 10.3 mmol) in CH₂Cl₂ (50 mL). The resulting mixture is stirred at room temperature for 3 hours, then washed with H₂O and concentrated. The residue is purified by flash chromatography. The resulting product is dissolved in 1,4-dioxane (200 mL) and an aqueous solution of 2M LiOH (200 mL) is dropped therein. After 24 h the solution is concentrated and acidified with 2M aq. HCl to pH 1.8 to precipitate the acid, which is filtered, washed with water and dried to give the desired product as a white solid (6.8 g; 4.5 mmol).
Yield: 44%
HPLC assay: 98.4% (in % area)
Elemental analysis:
% calc.: C 54.43; H 7.32; N 8.40;
% found: C 54.33; H 7.25; N 8.35.
$^1$H-NMR, $^{13}$C-NMR, IR and MS spectra are consistent with the indicated structure.

e) gadolinium complex of [3α[1(S),2(S)],5β,7α,12α]-3-[[[[cis-1,2-bis[[[5-[bis[2-[bis(carboxymethyl)amino]ethyl]amino]-5-carboxypentyl]amino]-carbonyl]-4-cyclopentyl]amino]carbonyl]oxy]-7,12-dihydroxycholan-24-oic acid salified with sodium (1:5).

The ligand from step d) (6 g; 4 mmol) is suspended in water and dissolved with NaOH. The resulting solution is added with GdCl$_3$ (2.97 g; 8 mmol) in H$_2$O (20 mL), keeping pH at 6.5 by addition of 1M NaOH. The mixture is kept 2 h at room temperature, then loaded on an Amberlite XAD® 16.00 column eluting with a CH$_3$CN/H$_2$O gradient. The fractions containing the product are evaporated to obtain the title compound as a white solid (6.7 g; 3.5 mmol).
Yield: 88%
M.p.: >300° C.
HPLC assay: 100% (in % area)
Elemental analysis:
% calc.: C 42.56; H 5.15; N 6.57; Gd 16.39; Na 5.99;
% found: C 42.42; H 5.10; N 6.45; Gd 16.28; Na 5.87.
IR and MS spectra are consistent with the indicated structure.

EXAMPLE 6

Following the procedure described in example 5, starting from cis-tetrahydro-1H-cyclopenta[c]furan-1,3,5-trione, 1,4,7-tris-[2-(1,1 dimethylethoxy)-2-oxoethyl]-10-[[2-[2-aminoethyl]amino]-2-oxoethyl]-1,4,7,10-tetraazacyclododecane (WO95/28967, example 2) and N$^2$,N$^2$-bis[2-[bis[2-(1,1-dimethylethoxy)-2-oxoethyl]amino]ethyl]-L-lysine tert-butyl ester (Bioconjugate Chem. 1999, 10, 137), the gadolinium complex of [3α[1(S)],5β,7α,12α]-3-[[[[cis-1-[[[5-[bis[2-[bis(carboxymethyl)amino]ethyl]amino]-5-carboxypentyl]amino]carbonyl]-2-[[[2-[[[4,7,10-tris(carboxymethyl)-1,4,7,10-tetraazacyclododec-I -yl]acetyl]amino]ethyl]-amino]carbonyl]-4-cyclopentyl]amino]carbonyl]oxy]-7,12-dihydroxycholan-24-oic acid was prepared.

EXAMPLE 7

Gadolinium complex of [3β[3(S),5(S)],5β,7α,12α]-3-[[[3,5-bis[[4-[bis[2-[bis(carboxymethyl)amino]ethyl]amino]-4-carboxy-1-oxobutyl]amino]phenyl]-carbonyl]amino]-7,12-dihydroxycholan-24-oic acid salified with sodium (1:5)

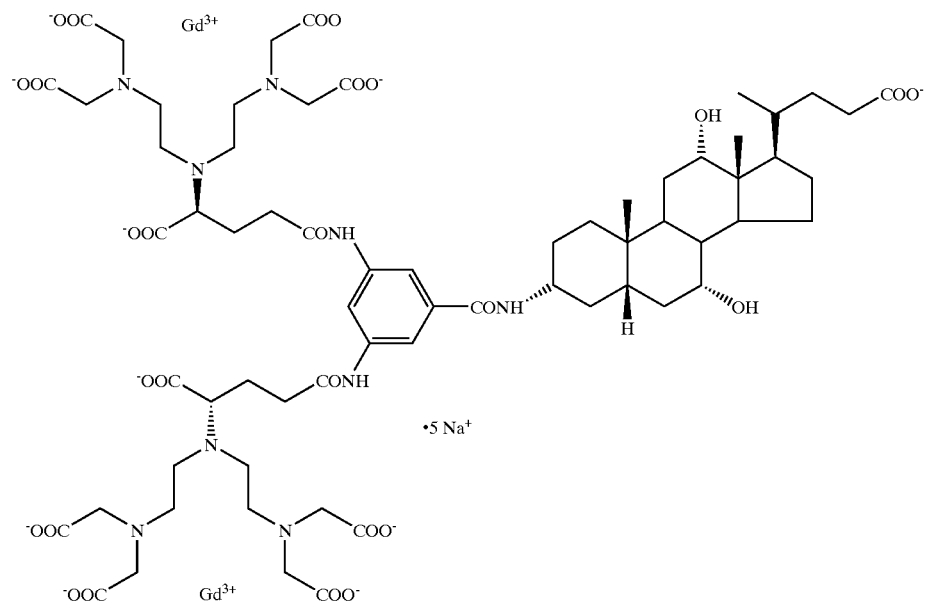

a) (3β,5β,7α,12α)-3-[[(3,5-diaminophenyl)carbonyl]amino]-7, 12-dihydroxycholan-24-oic acid dihydrochloride methyl ester.

3,5-di(tert-butoxycarbonyl)aminobenzoic acid (3.16 g; 10 mmol) (prepared as described in Chem. Commun. 1998, 1629) is dissolved in DMF (150 mL) and the resulting solution is added, at 0° C., with triethylamine (3 mL) and diethylcyanophosphonate (1.8 g; 11 mmol) (commercial product). Into the resulting mixture, a solution of (3β,5β,7α,12α)-3-amino-7,12-dihydroxycholan-24-oic acid methyl ester (4.22 g; 10 mmol) (obtained as described in Synth. Commun. 1998, 28, 109) is dropped, in 30 min. After 8 h at room temperature, the solution is evaporated and the resulting residue is purified on silica gel by flash chromatography. The resulting product is treated with HCl-saturated MeOH (100 mL) to precipitate the title product as a white solid (2.7 g; 4.3 mmol).
Yield: 43%
HPLC assay: 97% (in % area)
Elemental analysis:
% calc.: C 61.14; H 8.18; N 6.68; Cl 11.28;
% found: C 60.98; H 8.11; N 6.59; Cl 11.22.
$^1$H-NMR, $^{13}$C-NMR, IR and MS spectra are consistent with the indicated structure.

b) [3β[3(S),5(S)],5β,7α,12α]-3-[[[3,5-bis[[4-[bis[2-[bis[2-(1,1-dimethylethoxy)-2-oxoethyl]amino]ethyl]amino]-5-(1,1-dimethylethoxy)-1,5-dioxopentyl]amino]phenyl]carbonyl]amino]-7,12-dihydroxycholan-24-oic acid.

A solution of the product from step a) (2.5 g; 4 mmol) in DMF, N,N-bis[2-[bis[2-(1,1-dimethylethoxy)-2-oxoethyl]amino]ethyl]-L-glutamic acid tert-butyl ester (3 g; 4 mmol) (Bioconjugate Chem. 1999, 10, 137) and diethylcyanophosphonate (0.72 g; 4.4 mmol), kept at 0° C., is dropwise added with triethylamine (0.7 mL). After 1 h at 0° C. and 5 h at room temperature, the reaction mixture is evaporated and the residue is purified by flash silica gel chromatography, to obtain the desired product as oil (5.79 g; 2.9 mmol).

Yield: 73%
HPLC assay: 98% (in % area)
Elemental analysis:
% calc.: C 64.18; H 9.10; N 4.94;
% found: C 64.03; H 8.99; N 4.95.
$^1$H-NMR, $^{13}$C-NMR, IR and MS spectra are consistent with the indicated structure.

c) [3β[3(S),5(S)],5β,7α,12α]-3-[[[3,5-bis[[4-[bis[2-[bis(carboxymethyl)amino]-ethyl]amino]-4-carboxy-1-oxobutyl]amino]phenyl]carbonyl]amino]-7,12-dihydroxycholan-24-oic acid.

Into a solution of the polyester from step b) (5.5 g; 2.8 mmol) in 1,4-dioxane (100 mL) is dropped, at room temperature, a 2M LiOH aqueous solution (100 mL). After 24 hours the solution is concentrated and added with 2M aq. HCl to final pH 1.8 to precipitate the acid which is filtered, washed with water and dried to obtain the title product as a white solid (3.6 g; 2.2 mmol).

Yield: 80%
HPLC assay: 99% (in % area)
Elemental analysis:
% calc.: C 61.92; H 5.93; N 5.95;
% found: C 61.85; H 5.88; N 5.90.
$^1$H-NMR, $^{13}$C-NMR, IR and MS spectra are consistent with the indicated structure.

d) gadolinium complex of [3β[3(S),5(S)],5β,7α,12α]-3-[[[3,5-bis[[4-[bis[2-[bis(carboxymethyl)amino]ethyl]amino]-4-carboxy-1-oxobutyl]amino]phenyl]carbonyl]amino]-7,12-dihydroxycholan-24-oic acid salified with sodium (1:5).

The ligand from step c) (3.5 g; 2.1 mmol) is suspended in H$_2$O and dissolved by addition of 1M NaOH. GdCl$_3$ (1.56 g; 4.2 mmol) in H$_2$O (20 mL) is then dropped into the solution, keeping pH at 6.8 by addition of 1M NaOH. The mixture is stirred for 4 h at room temperature then loaded on an Amberlite XAD® 16.00 column eluting with a CH$_3$CN/H$_2$O gradient. The fractions containing the product are evaporated to obtain the title compound as a white solid (4.1 g; 2 mmol).

Yield: 95%
M.p.: >300° C.
HPLC assay: 100% (in % area)
Elemental analysis:
% calc.: C 49.39; H 4.19; N 4.74; Gd 15.21; Na 5.56;
% found: C 49.27; H 4.02; N 4.70; Gd 15.18; Na 5.48.
IR and MS spectra are consistent with the indicated structure.

EXAMPLE 8

Pharmacokinetics Screening in Rats

Materials and Methods

The experimentation was performed with the complex compound of example 1.

The screening was performed in 3 anaesthetised CD(SD) BR male rats (Charles River Italia).

The animals were maintained according to EEC Council Directive 86/605 as included in Italian law DL116/92 (experimental typology KIN 3).

The contrast agent was injected in the vena saphena at the single dose of 0.1 mmol.kg$^{-1}$, injection rate of 6 mL·min$^{-1}$.

After the administration of the complex compound, the collection of the biological fluids in the anaesthetised rats was performed by cannulation of urinary bladder and biliary duct. The urine was collected at 0 to 60, 60 to 120, 120 to 240, 240 to 480 min after injection; the bile at −30 to 0, 0 to 15, 15 to 30, 30 to 60, 60 to 120, 120 to 240, 240 to 480 min after injection.

Animals were killed at the end of the studies by exanguination from abdominal aorta.

Blood, liver and kidneys were collected after the sacrifice for the assay of gadolinium by inductively coupled plasma atomic emission ICP-AES.

Results

After intravenous administration to anaesthetised rats, gadolinium was eliminated both with urine and in trace amount with bile. In the 0 to 480 min period, biliary and urinary excretion accounted for 0.175% and 36% of ID, respectively. At 480 min after administration, the residual content in liver, kidney and plasma was 2.564%, 6.7%, and 14.3% of the injected dose, respectively.

| Collection time | Biliary % of the injected dose | Urinary % of the injected dose |
| --- | --- | --- |
| 0 to 15 min | 0.0102 ± 0.0010 | |
| 0 to 30 min | 0.0208 ± 0.0012 | |
| 0 to 60 min | 0.0374 ± 0.0023 | 11.2 ± 4.6 |
| 0 to 120 min | 0.0561 ± 0.0052 | 18.6 ± 5.0 |
| 0 to 240 min | 0.0950 ± 0.0073 | 27.9 ± 5.3 |
| 0 to 480 min | 0.175 ± 0.020 | 36.2 ± 2.7 |

What is claimed is:

1. A compound of formula (I):

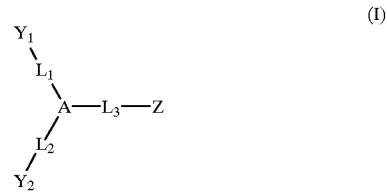

wherein:

A is a polyfunctional substrate selected from the following;

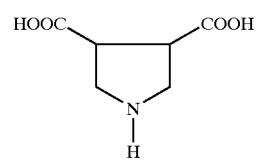

-continued
2
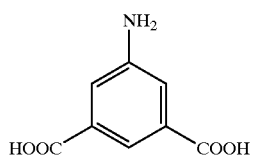
3
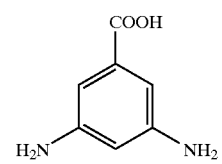
4
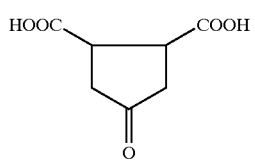
5
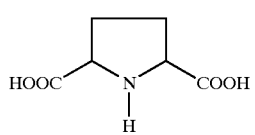
6
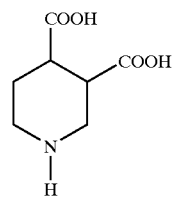
7
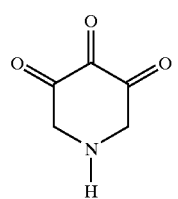
8
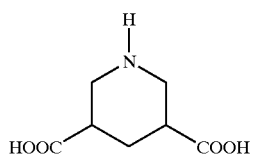
9
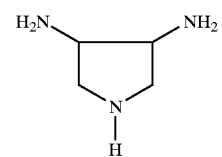
10
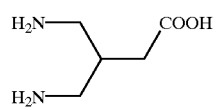
11
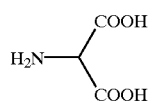
-continued
12
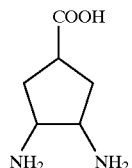
13
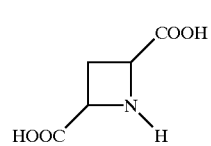
14
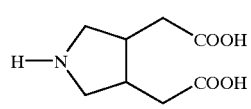
15
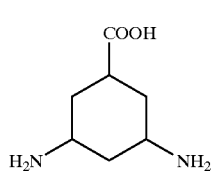
16
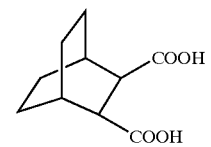
17
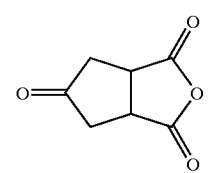
Z is a bile acid residue or a conjugate with taurine and glycine;
$Y_1$ and $Y_2$, which can be the same or different, are selected from the following:
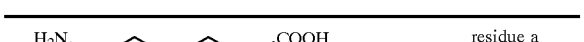
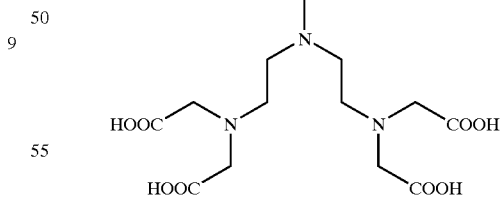
residue a
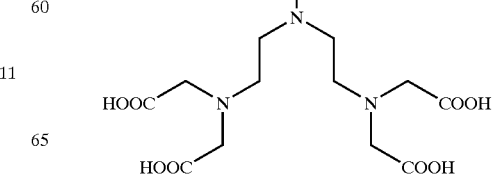
residue b -continued

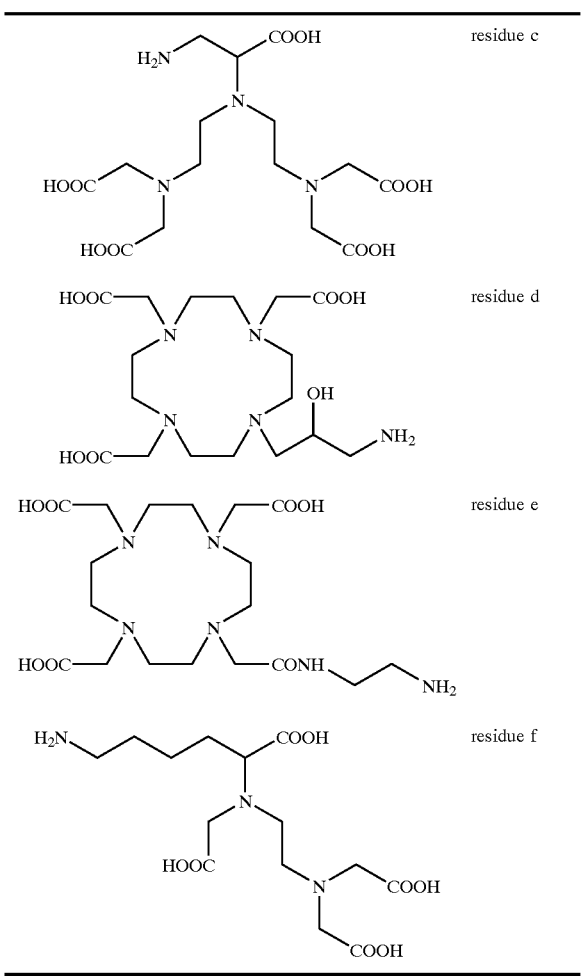

residue c residue d residue e residue f $L_1$, $L_2$ and $L_3$, which can be the same or different, are a single bond between the functional groups of $Y_1$ and A, $Y_2$ and A and/or Z and A, or a spacer chain with at most 20 carbon atoms;

as well as a complex chelate thereof with the ions of metal elements having atomic numbers ranging between 20 and 31, 39, 42, 43, 44, 49, and between 57 and 83, and a salt thereof with an organic base selected from primary, secondary, tertiary amines or basic amino acids, or with an inorganic base the cations of which are sodium, potassium, magnesium, calciuin or mixtures thereof, or with anions of physiologically acceptable organic or inorganic acids;

wherein linking between A and $Y_1$ and $Y_2$ is between a functionalized amino group present on $Y_1$ and $Y_2$ and a carboxylic residue present on A or between a carboxylic residue of $Y_1$ and $Y_2$ and an amino residue of A to form an amide and wherein linking between A and the bile acid residue Z is by formation of an amido bond.

2. A compound as claimed in claim 1 wherein $L_1$ and $L_2$, which can be the same or different, are a spacing chain of formula (II)

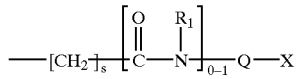 (II)

wherein:

Q is a $C_1$-$C_8$ alkyl chain optionally substituted with 1 to 3 OH groups;

s is an integer of 0 to 5;

$R_1$ is an H atom, or a $C_1$-$C_5$ alkyl group;

X is

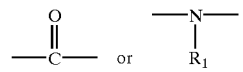

$L_3$ is a group of formula (III)

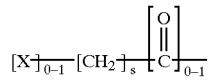 (III)

in which:

X and s have the above defined meanings with the proviso that when s is different from 0 then CO and X are present.

3. A compound as claimed in claim 1 in which $L_1$ and $L_2$, which can be the same or different, are selected from those of formulae (IV), (V), (VI)

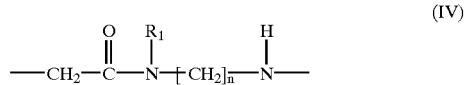 (IV)

 (V)

 (VI)

wherein:

$R_1$ is an H atom, or a $C_1$-$C_5$ alkyl group and n is an integer of 1 to 8 and $L_3$ is a single bond between Z and A or a group

4. A compound as claimed in claim 1 in which Z is a bile acid residue selected from one of the following:

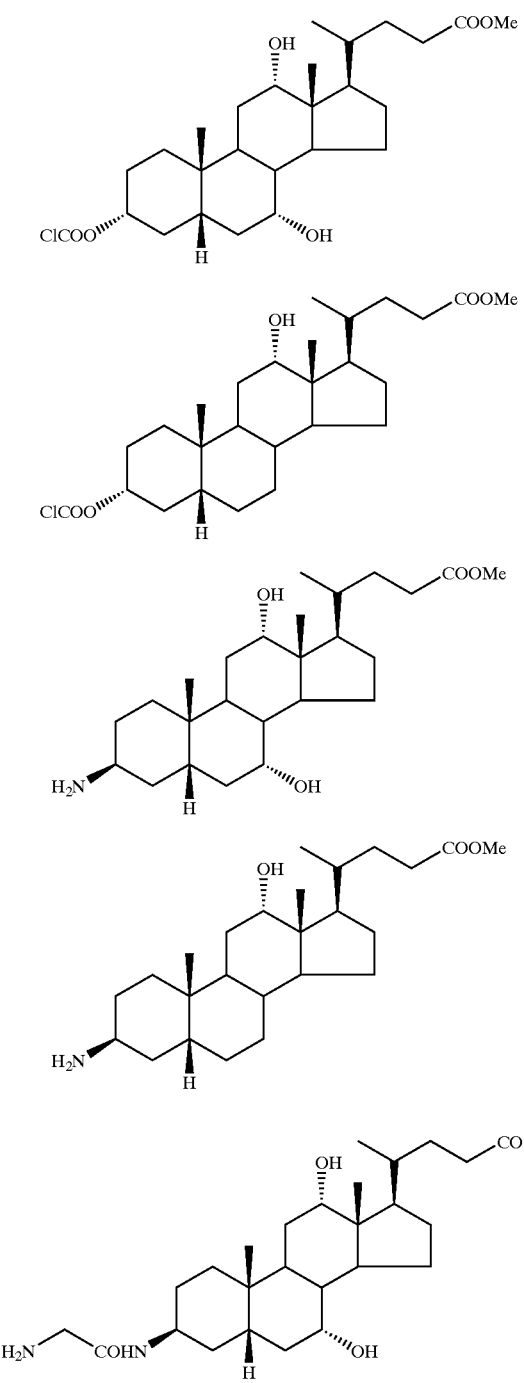

5. A compound as claimed in claim 1, in which the bile acid residue Z is a cholic acid residue.

6. A compound as claimed in claim 1 selected from the following:

[3α[3(S),4(S)],5β,12α]-3-[[[trans-3,4-bis[[[5-[bis[2-[bis(carboxymethyl)amino]ethyl]amino]-5-carboxypentyl]amino]carbonyl]-1-pyrrolidinyl]carbonyl]oxy]-12-hydroxycholan-24-oic acid;

[3α[3(S),4(S)],5β,12α]-3-[[[trans-3,4-bis[[[2-[bis[2-[bis(carboxymethyl)amino]ethyl]amino]-2-carrboxyethyl]amino]carbonyl]-1-pyrrolidinyl]-carbonyl]oxy]-12-hydroxycholan-24-oic acid;

(3α,5β,12α)-3-[[[-trans-3,4-bis[[[2-[[[4,7,10-tris(carboxymethyl)-1,4,7,10-tetraazacyclododec-1-yl]acetyl]amino]ethyl]amino]carbonyl]-1-pyrrolidinyl]carbonyloxy]-12-hydroxycholan-24-oic acid;

[3α[3(S),4(S)],5β12α]-3-[[[trans-3,4-bis[[[5-[[2-[bis(carboxy-methy)amino]-ethyl](carboxymetyl)amino]-5-carboxypentyl]amino]carbonyl]-1-pyrrolidinyl]carbo-nyl]oxy]-12-hydroxycholan-24-oic acid;

[3α[1(S),2(S)],5β,7α,12α]-3-[[[[cis-1,2-bis[[[5-[2-[bis(carboxmethyl)amino]amino]-5-carboxypentyl]amino]carbonyl]-4-cyclα-pentyl]amino]carbonyl]-oxy]-7,12-dihydroxycholan-24-oic acid;

[3α[1(S)]5β,7α,12α]-3-[[[[cis-1-[[[5-[bis[2-[bis(carboxymethyl)amino]ethyl]-amino]-5-carboxypentyl]amino]carbonyl]-2-[[[2-[[[4,7,10-tris(carboxymethyl)-1,4,7,10-tetraazacycylododec-1-yl]acetyl]amino]ethyl]amino]-carbonyl]-4-cyclo-pentyl]amino]carbonyl]oxy]-7,12-dihydroxycholan-24-oic acid;

[3β[3(S),5(S)],5β,7α,12α]-3-[[[3,5-bis[[4-[bis[2-[(bis(carboxymethyl)amino]-ethyl]amino]-4-carboxy-1-oxobutyl]amino]phenyl]carbonyl]amino]-7,12-dihydroxy-cholan-24-oic acid.

7. A compound as claimed in claim 1 wherein the bi- or trivalent metal ions complexed with the chelant residues $Y_1$ and $Y_2$ are selected from $Fe^{(2+)}$, $Fe^{(3+)}$, $Gd^{(3+)}$, $Eu^{(3+)}$, $Dy^{(3+)}$, $La^{(3+)}$, $Yb^{(3+)}$ and $Mn^{(2+)}$.

8. A compound as claimed in claim 1 wherein the salifying organic base is selected from etbanolamine, diethanolamine, niorpholine, glucamine, N,N-dimethylglucamine, N-methylglucamine, lysine, arginine, ornithine.

9. A compound as claimed in claim 1 wherein the anion of the salifying inorganic acid is selected from halo acid ions such as iodides, bromides and chlorides.

10. A diagnostic contrastographic pharmaceutical composition comprising at least one of the chelates as claimed in claim 1 or a physiologically compatible salt thereof.

11. method of magnetic resonance imaging the organs or tissues of a human or animal body comprising providing a chelate of claim 1 or a physiologically compatible salt thereof and magnetic resonance imaging the subject to visualize the organs or tissues.

12. The method of claim 11 in which the vascular system is visualized.

13. The method of claim 12 in which the coronary vasculature is visualized.

* * * * *